United States Patent
Blood et al.

(10) Patent No.: US 6,228,985 B1
(45) Date of Patent: May 8, 2001

(54) DERIVATIVES OF AMINOBENZOIC AND AMINOBIPHENYLCARBOXYLIC ACIDS USEFUL AS ANTI-CANCER AGENTS

(75) Inventors: Christine H. Blood, Morristown; Bernard R. Neustadt, West Orange; Elizabeth M. Smith, Verona, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/082,787

(22) Filed: May 21, 1998

(51) Int. Cl.$^7$ .................. C07K 2/00; A61K 38/00; C07C 233/00; C07C 229/00; C07D 209/20

(52) U.S. Cl. .................. 530/300; 548/496; 562/450; 564/157

(58) Field of Search .................. 548/496; 530/300; 562/450; 564/157

(56) References Cited

U.S. PATENT DOCUMENTS 5,646,285 * 7/1997 Baindur et al. .................. 546/298

FOREIGN PATENT DOCUMENTS

| WO 96/00730 | 1/1996 | (WO). |
| WO 96/40747 | 12/1996 | (WO). |
| WO 97/06791 | 2/1997 | (WO). |

OTHER PUBLICATIONS

Neustadt et al. Construction of a Family of Biophenyl Combinatorial Libraries: Structure–Activity Studies Utilizing Libraries of Mixtures. Bioorganic & Medicinal Chemistry Letters. 1998, vol. 8, pp. 2395–2398, 1998.*

Ploug et al. Ligan Interaction between Urokinase–Type Plasminogen Activator and Its Receptor Probed with 8–Anilino–1–naphthalenesulfonate. Evidence for a Hydrophobic Binding Site Exposed Only on the Intact Receptor. Biochemistry. 1994, vol. 33, pp. 8991, 1994.*

Behrendt et al. Binding of the Urokinase–type Plasminogen Activator to Its Cell: Surface Receptor is Inhibited by Low Doses of Suramin. The Journal of Biological Chemistry. Mar. 1993, vol. 268, No. 8, pp. 5985–5989.*

* cited by examiner

Primary Examiner—Howard C. Lee
Assistant Examiner—Everett White
(74) Attorney, Agent, or Firm—William Lee; Arthur Mann

(57) ABSTRACT

The present invention provides compounds having the formula:

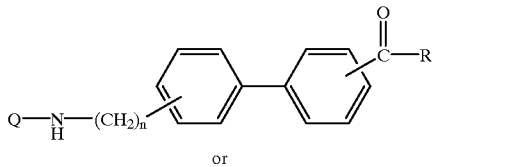

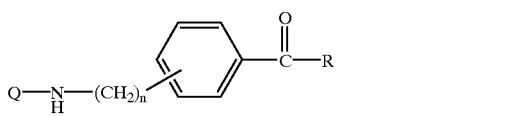

wherein n is 0 or 1;
R is —NH$_2$ or

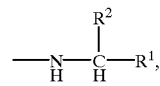

wherein $R^1$ and $R^2$ are independently selected from the group consisting of H, alkyl, aralkyl, heteroaralkyl, carboxy, carboxyalkyl, and carbamoyl;

Q is $R^3C(O)$— or

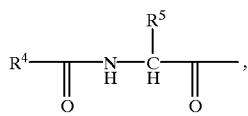

wherein $R^5$ is selected from the
group consisting of H, alkyl, aralkyl, heteroaralkyl, and carbamoylalkyl, and $R^3$ and $R^4$ are selected from the group consisting of H, alkyl, alkoxy, arylalkoxy, aralkyl, heteroaralkyl, and carbamoylalkyl;

the Q—NH—(CH$_2$)$_n$— and the —C(O)R substituents of the compound of formula I are independently positioned ortho, meta, orpara relative to the carbon atoms that form the bond between the two phenyl groups to which said substituents are bound, with the proviso that said substituents are not both positioned ortho; and the Q—NH—(CH$_2$)$_n$ and the —C(O)R substituents of the compound of formula II are positioned meta orpara to each other;

or a biolabile ester thereof, or a pharmaceutically acceptable salt thereof. The compounds are useful for treating uPA- or uPAR-mediated disorders, e.g., tumor metastasis, tumor angiogenesis, restenosis, chronic inflammation, or corneal angiogenesis.

9 Claims, No Drawings

DERIVATIVES OF AMINOBENZOIC AND AMINOBIPHENYLCARBOXYLIC ACIDS USEFUL AS ANTI-CANCER AGENTS

FIELD OF THE INVENTION

This invention relates to compounds that inhibit the interaction of urokinase-type plasminogen activator (uPA) with urokinase-type plasminogen activator receptor (uPAR), and methods for using such compounds to treat uPA or uPAR mediated disorders, e.g., cancer.

BACKGROUND OF THE INVENTION

Urokinase-tpe plasminogen activator (uPA) is a multidomain serine protease, having a catalytic "B" chain (amino acids 144–411), and an amino-terminal fragment ("ATF", aa 1–143) consisting of a growth factor-like domain (4–43) and a kringle (aa 47–135). The uPA kringle appears to bind heparin, but not fibrin, lysine, or aminohexanoic acid. The growth factor-like domain bears some similarity to the structure of epidermal growth factor (EGF), and is thus also referred to as an "EGF-like" domain. The single chain pro-uPA is activated by plasmin or other proteases, cleaving the chain into the two-chain active form, which is linked together by a disulfide bond.

uPA binds to its specific cell surface receptor (uPAR). The binding interaction is apparently mediated by the EGF-like domain (S. A. Rabbani et al., *J Biol Chem* (1992) 267:14151–56). Cleavage of pro-uPA into active uPA is accelerated when pro-uPA and plasminogen are receptor-bound. Thus, plasmin activates pro-uPA, which in turn activates more plasmin by cleaving plasminogen. This positive feedback cycle is apparently limited to the receptor-based proteolysis on the cell surface, since a large excess of protease inhibitors is found in plasma, including $\alpha_2$ antiplasmin, and PAI-1.

Plasmin can activate or degrade extracellular proteins such as fibrinogen, fibronectin, and zymogens, particularly of the matrix metalloproteinases. Plasminogen activators thus can regulate extracellular proteolysis, fibrin clot lysis, tissue remodeling, developmental cell migration, inflammation, and metastasis. Accordingly, there is great interest in developing uPA inhibitors and uPA receptor antagonists. E. Appella et al., *J Biol Chem* (1987) 262:4437–40, determined that receptor binding activity is localized in the EGF-like domain, and that residues 12–32 appear to be critical for binding. The critical domain alone ($uPA_{12-32}$) bound uPAR with an affinity of 40 nM (about 100 fold less than intact ATF).

Recent studies have shown that the invasiveness of human tumor cell lines in vitro correlates with surface bound urokinase, and that urokinase production itself is an independent prognostic indicator in human breast cancer (W. Schlechte et al., *Cancer Comm* (1990) 2:173–79; H. Kobayashi et al., *Br J Cancer* (1993) 67:537–44; J. A. Foekens et al., *Cancer Res* (1992) 52:6101–05). It has also been shown in both breast and colon cancer that urokinase is often made by stromal cells (fibroblasts and macrophages), whereas the urokinase receptor is found on tumor cells (C. Pyke et al., *Cancer Res* (1993) 53:1911–15; C. Pyke et al., *Am J Path* (1991) 138:1059–67). uPAR has independently been identified as a monocyte activation antigen, Mo3, whose expression is induced in these inflammatory cells upon activation (H. Y. Min et al., *J Immunol* (1992) 148:3636–42), as well as an activation antigen on human T lymphocytes (A. Nykjaer et al., *J Immunol* (1994) 152:505–16). Urokinase plasminogen activator "knockout" mice (in which the uPA gene is inactivated or deleted throughout the body) have been developed, and their macrophages are deficient in extracellular matrix degradation in vitro (P. Carmeliet et al., *Fibrinolysis* (1993) 7 *Suppl.* 1:27–28). In addition, these mice show greatly reduced smooth muscle cell migration/proliferation after arterial wounding, suggesting a possible role for uPA/uPAR in post-angioplasty restenosis.

The induction of urokinase and its receptor by agents known to be angiogenic in vivo, such as bFGF, vEGF, and TNFα, suggests a role for cell surface urokinase in angiogenesis (P. Mignatti et al., *J Cell Biol* (1991) 113:1193–202; L. E. Odekon et al., *J Cell Physiol* (1992) 150:258–63; M. J. Niedbala et al., *Blood* (1992) 79:678–87). Although many factors are likely to be angiogenic in pathological conditions, degradation of extracellular matrix by capillary endothelial cells and release of matrix-bound proangiogenic factors by cell surface plasmin is likely a common step in these processes (D. Weinstat-Saslo et al., *FASEB J* (1994) 8:401–07). This is further supported by the observation that several known anti-angiogenic substances reduce uPA expression (S. Tankano et al., *Cancer Res* (1994) 54:2654–60). In vivo studies have shown that prevention of urokinase-receptor binding, by urokinase antibodies or competition with inactive urokinase mutants, dramatically reduces or eliminates the metastatic potential of human prostate tumor cells in nude mice (C. W. Crowley et al., *Proc Natl Acad Sci USA* (1993) 90:5021–25; L. Ossowski et al., *Cell* (1983) 35:611–19; L. Ossowski, *J Cell Biol* (1988) 107:2437–45). It has recently been shown in both in vitro and syngeneic in vivo models that the protein uPAR antagonists are anti-angiogenic (Min et al., *Cancer Res* (1996) 56:2428).

Although a primary role of uPAR is in the focusing of uPA dependent plasmninogen activation to the cell surface, it also has other functions. For instance, uPAR is involved in cell adhesion, functioning as a uPA dependent vitronectin receptor (Wei et al., *J Biol Chem* (1994) 269:32380–88). More recently, it has been shown that uPAR interacts with integrins and is likely involved in cell shape changes and cell migration (Kindzelskii et al., *J Immunol* (1996) 156:297).

Two small molecules have been described which inhibit the uPA:uPAR interaction (suramin: N. Behrendt et al., *J Biol Chem* (1993) 68:5985–89; and 8-anilinonaphthalene sulfonic acid: M. Ploug et al., *Biochemistry* (1994) 33:8991–97). Other compounds for inhibiting the uPA:uPAR interaction are described in International Publication No. WO 96/40747, published Dec. 19, 1996.

SUMMARY OF THE INVENTION

We have invented novel compounds having a high affinity for uPAR, thereby inhibiting the uPA:uPAR interaction, making them useful for treating disorders or diseases mediated by uPA and/or uPAR. The compounds of our invention have the formula

I

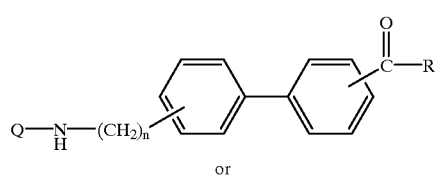

or

-continued

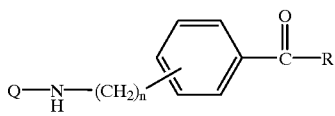

wherein n is 0 or 1;
R is —NH$_2$ or

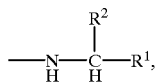

wherein R$^1$ and R$^2$ are independently selected from the group consisting of H, alkyl, aralkyl, heteroaralkyl, carboxy, carboxyalkyl, and carbamoyl;

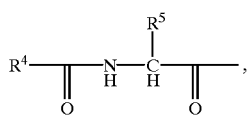

wherein R$^5$ is selected from the group consisting of H, alkyl, aral:yl, heteroaralkyl, and carbamoylalkyl, and R$^3$ and R$^4$ are selected from the group consisting of H, alkyl, alkoxy, arylalkoxy, aralkyl, heteroaralkyl, and carbamoylalkyl;

the Q-NH—(CH$_2$)$_n$— and the —C(O)R substituents of the compound of formula I are independently positioned ortho, meta, or para relative to the carbon atoms that form the bond between the two phenyl groups to which said substituents are bound, with the proviso that said substituents are not both positioned ortho; and the Q-NH—(CH$_2$)$_n$— and the —C(O)R substituents of the compound of formula II are positioned meta or para to each other;

or a biolabile ester thereof, or a pharmaceutically acceptable salt thereof.

Such compounds are useful for treating mammals, preferably humans, afflicted with disorders or diseases mediated by uPA and/or uPAR.

DETAILED DESCRIPTION OF THE INVENTION

R$^1$ and R$^2$ are preferably selected from the group consisting of H, benzyl, —CH$_2$C(O)OH, p-hydroxybenzyl, —C(O)OH, —C(O)NH$_2$, and

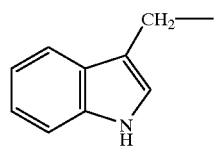

More preferably, R is selected from the group consisting of —NH$_2$, —Phe—OH, —Asp—OH, —β—Ala—OH, —Phe—NH$_2$, —D—Phe—OH, —Asp—NH$_2$, —Tyr—OH, —Trp—OH, and

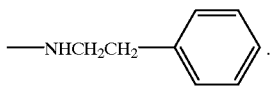

R$^3$ is preferably selected from the group consisting of methoxy and

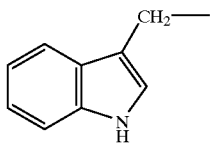

R$^4$ is preferably selected from the group consisting of methyl or

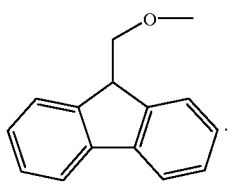

R$^5$ is preferably selected from the group consisting of benzyl, —CH$_2$CH$_2$C(O)NH$_2$, and

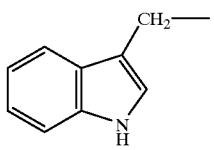

More preferably, Q is selected from the group consisting of CH$_3$C(O)—Trp—, CH$_3$C(O)—D—Trp—, Fmoc—Trp—, CH$_3$OC(O)—,

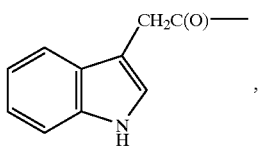

CH$_3$C(O)—Phe—, and CH$_3$C(O)—Gln—.

Examples of preferred compounds within the scope of the present invention include:

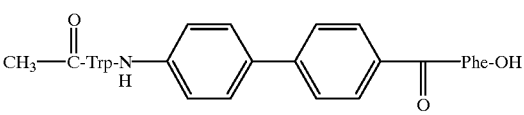

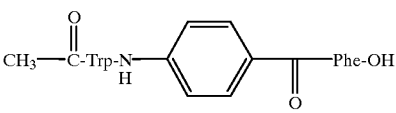

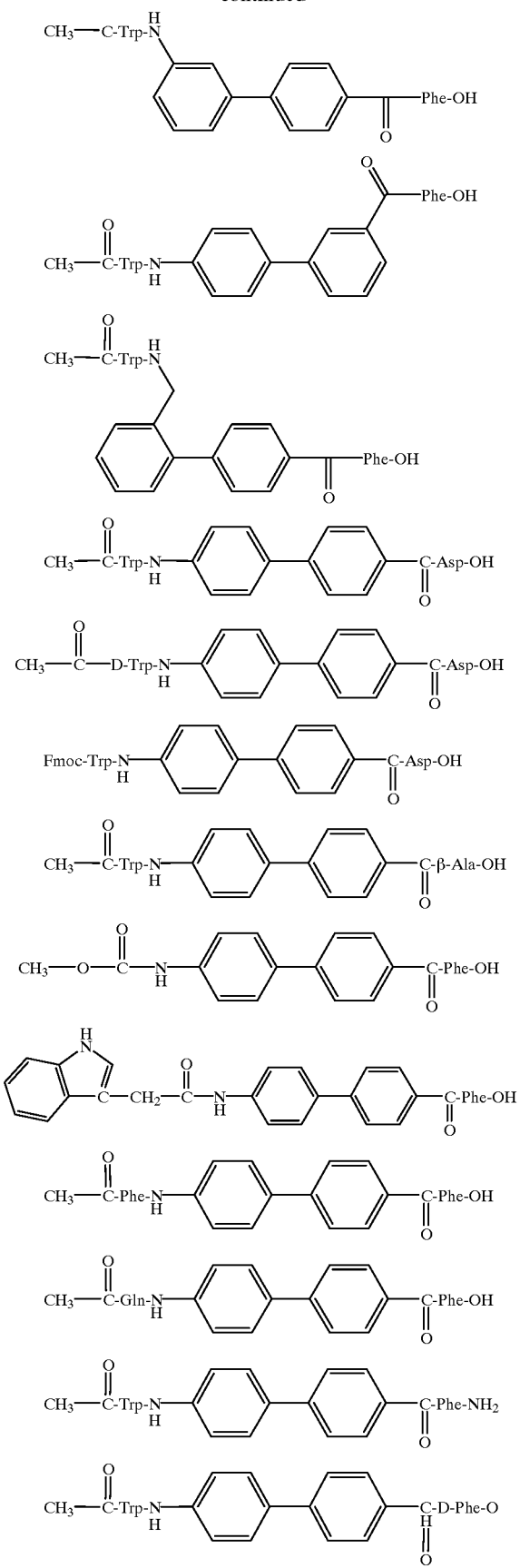
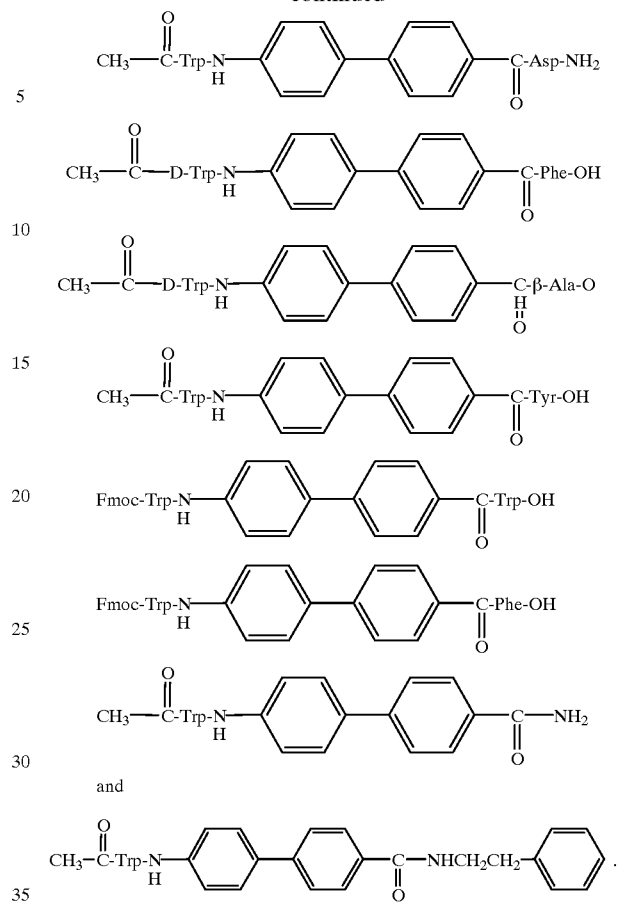
and
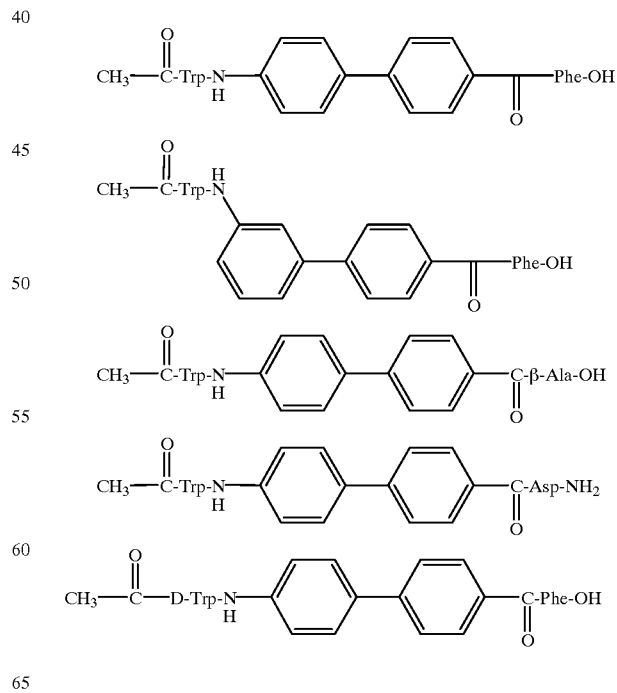
Of the foregoing compounds, the following are particularly preferred:
As used herein, the following terms have the following meanings, unless defined otherwise:

"Alkyl" refers to straight or branched hydrocarbon chain groups having 1 to 20 carbon atoms, preferably, 1 to 6 carbon atoms.

"Alkoxy" refers to groups having the formula —OR, wherein R is alkyl.

"Aryl" refers to carbocyclic groups having at least one aromatic ring.

"Aralkyl" refers to groups having the formula aryl—R—, wherein R is alkyl.

"Heteroaryl" refers to aromatic carbocyclic groups, wherein one or more of the carbon atoms of such groups are replaced with a heteroatom selected from O, S and N.

"Heteroaralkyl" refers to groups having the formula heteroaryl—R—, wherein R is alkyl.

"Arylalkoxy" refers to groups having the formula aryl—R—O—, wherein R is alkyl.

"Carboxy" refers to a group having the formula —C(O)OH.

"Carboxyalkyl" refers to groups having the formula, —R—C(O)OH, wherein R is alkyl.

"Carbamoyl" refers to a group having the formula —C(O)NH$_2$.

"Carbamoylalkyl" refers to groups having the formula —R—C(O)NH$_2$, wherein R is alkyl.

The following abbreviations are used herein to represent certain amino acids:

"Phe" refers to phenylalanine.

"Asp" refers to aspartic acid.

"β-Ala" refers to falanine.

"Tyr" refers to tyrosine.

"Trp" refers to tryptophan.

"Gln" is glutamine.

"D-Trp" is tryptophan in the D-configuration.

As used herein, the depiction of a bond on the right side of one of the abbreviations for the foregoing amino acids represents a bond to the carboxyl-terminal carbonyl atom of the amino acid and a bond on the left side of one of the abbreviations for the foregoing amino acids represents a bond to the nitrogen atom of the amino-terminal portion of the amino acid. For example,

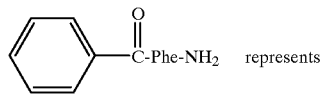 represents

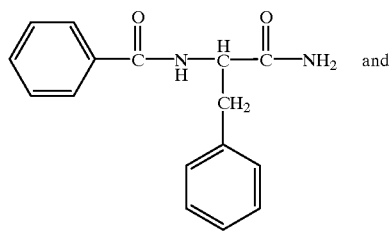 and

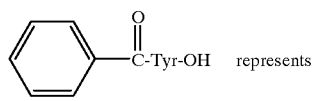 represents

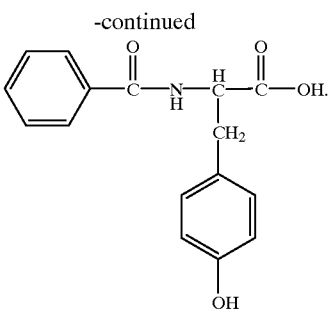

"Fmoc" refers to 9-fluorenylmethoxycarbonyl.

The term "biolablile ester" means a pharmaceutically acceptable, biologically degradable ester derivative of a compound of formula (I) or (II), that is a prodrug which, upon administration to a animal or human being, is converted in the body to a compound of formula (I) or (II).

The term "uPA -or uPAR—mediated disorder" refers to a disease state or malady which is caused or exacerbated by a biological activity of uPA or uPAR. The primary biological activity exhibited is plasminogen activation. Disorders mediated by plasminogen activation include, without limitation, inappropriate angiogenesis (e.g., diabetic retinopathy, corneal angiogenesis, Kaposi's sarcoma, and the like), metastasis and invasion by tumor cells, and chronic inflammation (e.g., rheumatoid arthritis, emphysema, and the like). Fucosylated ATF is also mnitogenic for some tumor cells (e.g., SaOS-2 osterosarcoma cells), which sometimes self-activate in an autocrine mechanism. Accordingly, the uPAR antagonist of the invention is effective in inhibiting the proliferation of uPA—activated tumor cells.

The term "effective amount" refers to an amount of uPAR antagonist compound sufficient to exhibit a detectable therapeutic effect. The therapeutic effect may include, for example, without limitation, inhibiting the growth of undesired tissue or malignant cells, inhibiting inappropriate angiogenesis, limiting tissue damage caused by chronic inflammation, and the like. The precise effective amount for a subject will depend upon the subject's size and health, the nature and severity of the condition to be treated, and the like. The effective amount for a given situation can be determined by routine experimentation based on the information provided herein.

The following abbreviations are used for the solvents and reagents discussed herein: ethanol ("EtOH"); methanol ("MeOH"); acetic acid ("AcOH"); ethyl acetate ("EtOAc"); 2-(1H-benzotriazole-1-yl)-1,1,3,3-tetramethyluronium hexafluorophosphate ("HBTU"); 1-hydroxybenzotriazole ("HOBt"); bromo-tris-pyrrolidino-phosphonium hexafluorophosphate ("PyBroP"); N,N-dimethylformarmide ("DMF"); trifluoroacetic acid ("TFA"); 1-(3-dimethylaminopropyl)-3-ethylcarbodiimide hydrochloride ("EDCI"); and diisopropylamine ("DIPEA"). In addition, "Ph" represents a phenyl group; "tBu" represents a —C(CH$_3$)$_3$ group; and "OtBu" represents an —O—C(CH$_3$)$_3$ group.

The compounds of the invention have asymmetric carbon atoms, and therefore, al. isomers, including enantiomers and diastereomers are within the scope of this invention. The invention includes d and l isomers in both pure form and in admixture, including racemic mixtures. Isomers can be prepared using conventional techniques, either by reacting chiral starting materials, or by separating isomers of compounds of formula (I) or (II).

Certain compounds of the present invention will be acidic in nature (e.g., those which have a carboxyl or phenolic hydroxyl group). These compounds form pharmaceutically acceptable salts with inorganic and organic bases. The salt may be prepared by treating a solution of the compound with the appropriate base. Non-limitative examples of such salts are sodium, potassium, calcium, aluminum, gold and silver salts, and salts formed with pharmaceutically acceptable amines such as ammonia, alkyl amines, hydroxyalkylamines, N-methylglucamine and the like.

It may be desirable when providing the compounds of the invention for oral administration to use the compounds of formula (I) or (II) in the form of a biolabile ester. The suitability of any particular ester-forming group can be assessed by conventional in vivo animal or in vitro enzyme hydrolysis studies. Thus, desirably, for optimum effect, the ester should only be hydrolysed after absorption is complete. Accordingly, the ester should be resistant to premature hydrolysis by digestive enzymes before absorption, but should be productively hydrolysed by, for example, gutwall, plasma or liver enzymes. In this way, the active acid is released into the bloodstream following oral absorption of the prodrug.

Suitable biolabile esters may include alkyl, alkanoyloxyalkyl, cycloalkanoyloxyalkyl, aroyloxyalkyl and alkoxycarbonyloxyalkyl esters, including cycloalkyl and aryl substituted derivatives thereof, aryl esters and cycloalkyl esters, wherein said alkyl, alkanoyl or alkoxy groups may contain from 1 to 8 carbon atoms and be branched-chain or straight-chain, said cycloalkyl groups may contain from 3–7 carbon atoms and said cycloalkanoyl groups from 4–8 carbon atoms wherein both are optionally benzo-fused, and said aryl and aroyl groups include substituted phenyl, naphthyl or indanyl ring systems. Preferably, the biolabile esters of the invention are $C_1$–$C_4$ alkyl esters. More preferably, they are methyl, ethyl and t-butyl esters.

Biolabile esters may be obtained from the acids of formula (I) or (II) by standard reactions well known to persons skilled in the art. For example, aryl and alkyl esters can be synthesized via activation of a carboxylic acid group of (I) in a variety of ways, such as by forming the acyl chloride, followed by reaction with the required phenol or alcohol. Alternatively, alkyl esters are obtainable by alkylation of a suitable alkali, or alkaline earth, metal carboxylate salt of a compound of formula (I) or (II).

The compounds of formula (I) may be prepared according to the following reaction scheme (Scheme I):

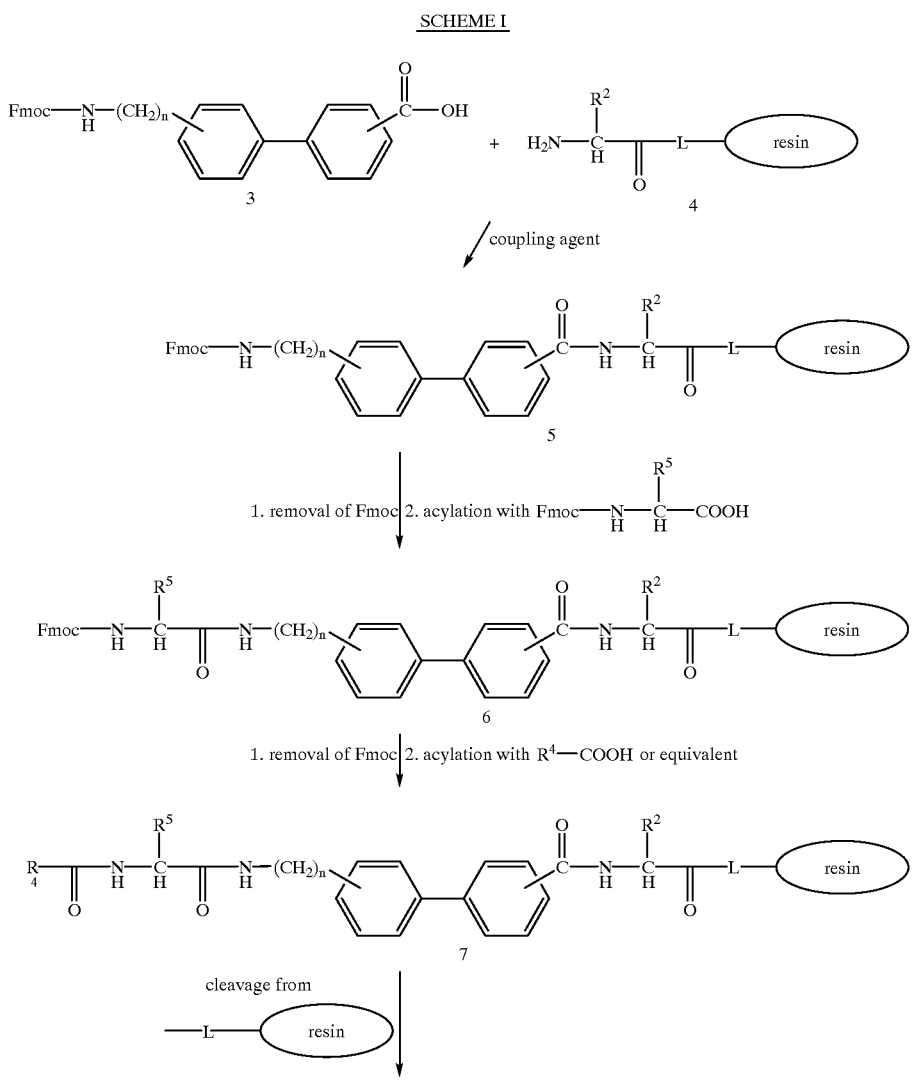

-continued

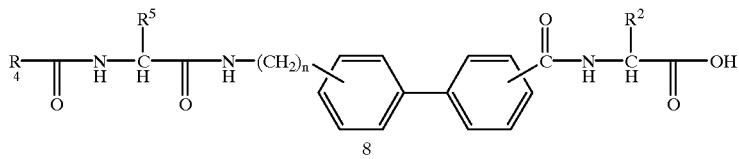

8

In Scheme I, which depicts a solid phase preparation, compound 3, wherein n is 0 or 1, is reacted with compound 4 and a coupling agent, e.g., HBTU/HOBt or PyBroP to form the amide compound 5. This reaction may be carried out in a suitable organic solvent, e.g., $CH_2Cl_2$ or DMF at temperatures of 0 to 80° C., with ambient temperature preferred. Resin 4 is a material having a ligand portion,

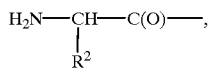

wherein $R_2$ is as previously defined for formula (I) above, bound to a resin, preferably a cross-linked polystyrene or a polyethylene glycol/polystyrene copolymer, through a cleavable linker, L, preferably an acid labile linker such as those used in SASRIN resin or in Wang resin. Other resins which may be used include, e.g., chlorotrityl resin and Rink Amide MBHA resin (where $R^1$ is carbamoyl). The aminoacid portion of 4 is attached to the linker by methods well known in the art, depending on the specific linker used. Generally, the amino group is protected in Fmoc form.

The Fmoc-group of amide compound 5 is then removed by conventional means, e.g., by treating with piperdine in DMF at 0 to 80° C., followed by acylation with Fmoc—NHCHR$^5$—COOH wherein $R^5$ is as previously defined for formula (I) above, to produce amide compound 6. The acylation is carried out employing the coupling reagents and reaction conditions described above. The Fmoc—NHCHR$^5$COOH compounds used in the acylation are either commercially available or preparable by known methods.

The Fmoc-group of amide compound 6 is removed, followed by acylation with $R^4$—COOH, wherein $R^4$ is as previously defined for formula (I) above, to produce compound 7, using the same Fmoc-removal and acylation methods used to make compound 6. Alternatively, equivalent reagents $R^4$—COCl and $[R^4CO]_2O$ may be employed instead of $R^4$—COOH, with the reaction conducted in $CH_2Cl_2$ or DMF at 0 to 80° C., in the presence of a tertiary amine, e.g., DIPEA.

Compound 8 is formed by cleavage from the linker and the resin portion of compound 7 by conventional means, e.g., by treating with dilute TFA in $CH_2Cl_2$ at ambient temperature for 10 to 60 minutes.

When it is desired to make compounds of formula (I) wherein Q is $R^3C(O)$—, the Fmoc-group of amide compound 5 can be removed, followed by acylation with $R^3$—COOH under the same conditions described above, and the resulting compound may be cleaved from the resin under the same conditions described above to produce the desired compound.

SCHEME II

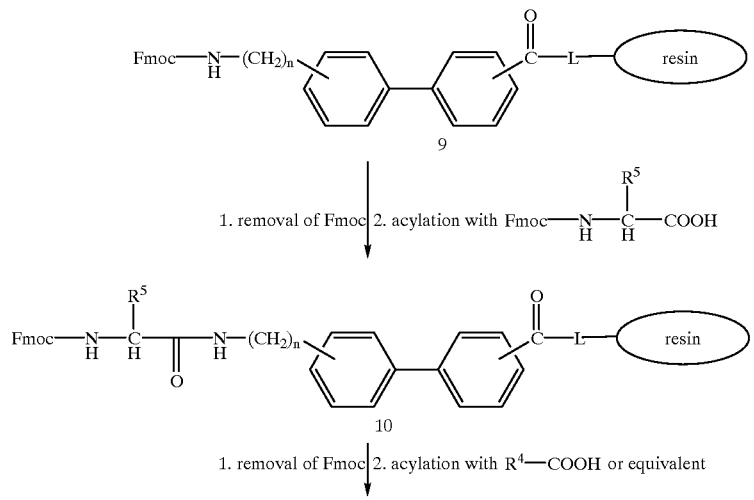

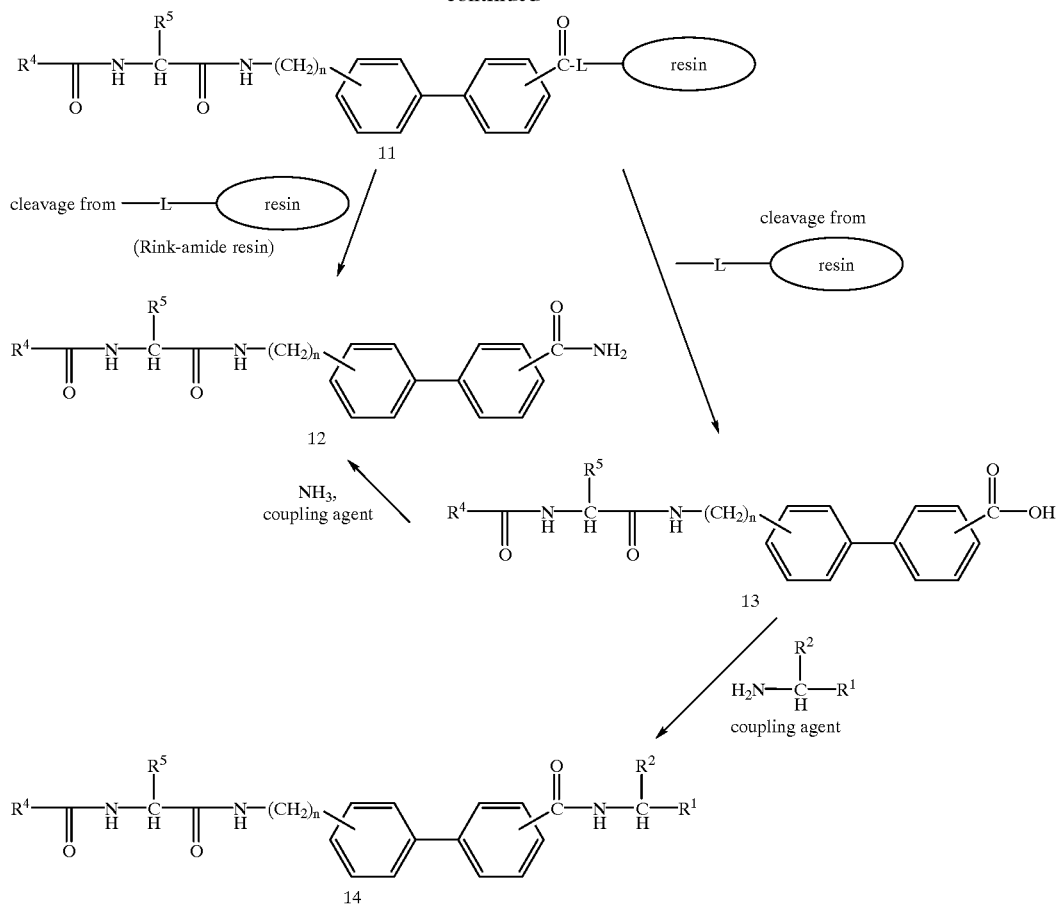

Scheme II depicts preparation of compounds wherein R is NH2 or $R^1$ and $R^2$ are H, alkyl, or aralkyl. In1 this scheme, attachment of 3 to the resin and linker provides resin 9. Subsequent steps as in Scheme I provide 11. When Rink amide linker is employed, cleavage of 11, typically with dilute TFA, affords amide 12. When a non-amide linker is present in 11, cleavage from the resin furnishes acid 13. Acid 13 may be converted to amide 12 by treatment with ammonia in the presence of an activating agent such as ethyl chloroformate. Alternatively, 13 may he converted to substituted amides 14 by treatment with a primary or secondary amine and a coupling agent such as EDCI.

Starting compound 3 may be prepared according to several different methods, which are shown below (as reaction schemes for preparation of starting compounds 3a, 3b, and 3c ). For the preparation of starting compound 3a, nitration of compound 20 with fuming nitric acid at 0° C. produces compound 21, which upon catalytic hydrogenation with $PtO_2$ in aqueous methanolic NaOH yields compound 22. The Fmoc group is introduced typically with Fmoc-chloride or Fmoc-hydroxysuccinimide ester in basic semi-aqueous medium, preferably in aqueous dioxane at 0° to 25° C. Where desired, a transient silyl ester may be employed for this step.

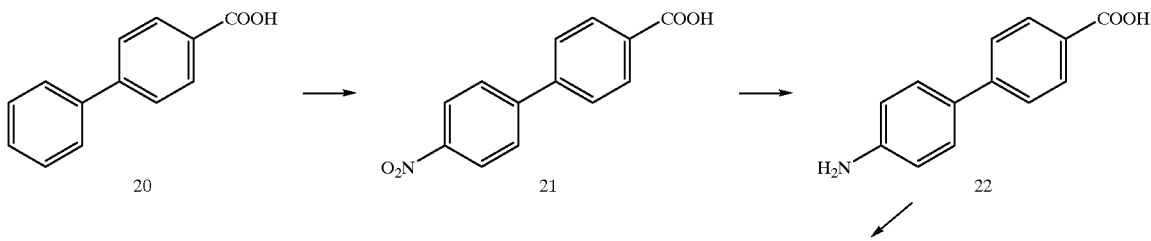

-continued

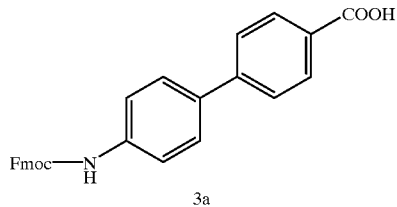

3a

In a second method, shown below, Pd-mediated coupling between 23 and 24 yields biphenyl ester 25. Preferably, this reaction is carried out with a Pd(P(Ph)$_3$)$_4$ catalyst in a toluene/aqueous Na$_2$CO$_3$ system at reflux. Saponification of compound 25, preferably with, alkali in aqueous methanol at 0° to 50° C., and reduction, preferably with Pd/C in aqueous. alkali, yield amino-acid 26, which may be converted as above to yield compound 3b.

coupled in a Pd-mediated reaction as above to yield compound 29. Compound 29 is reacted with N-bromosuccinimide in CCl$_4$ at reflux to yield bromide 30, which is converted to ester 31 by reaction with NaN$_3$ in DMF at ambient temperature, followed by hydrogenation

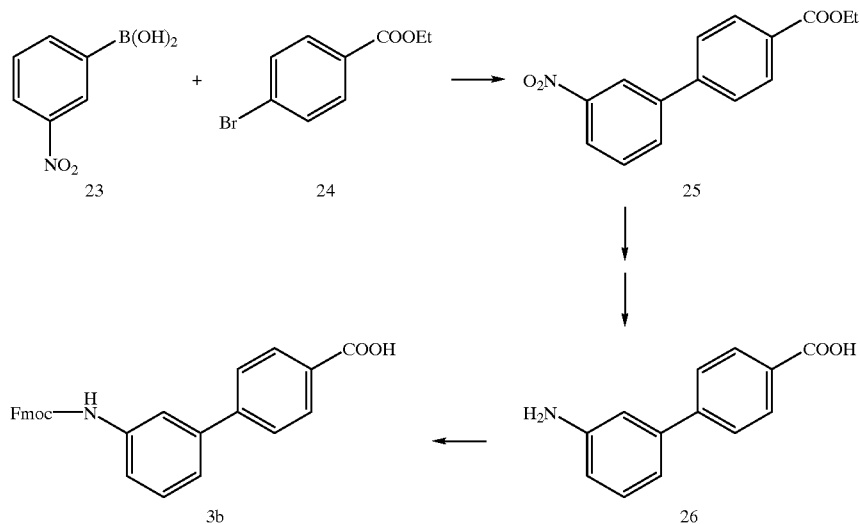

When n=1, compound 3c may be prepared by the following method, shown below. Compounds 27 and 28 are with Pd/C in ethanol. Conversion of the ester 31 to Fmoc-acid 3c is cared out as described above.

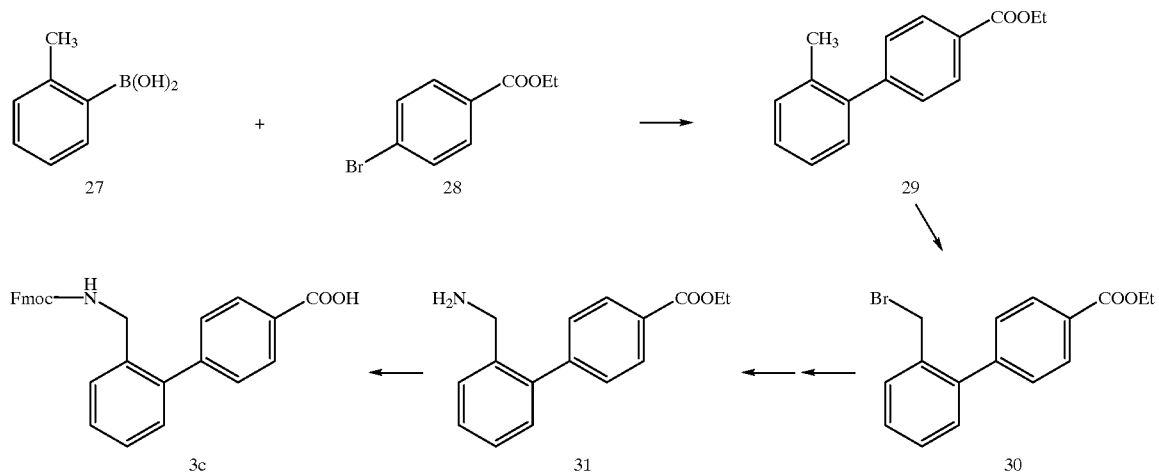

As an alternative to Scheme I, compounds of formula (I) may be prepared by a solution synthesis as shown in Scheme III, below:

SCHEME III

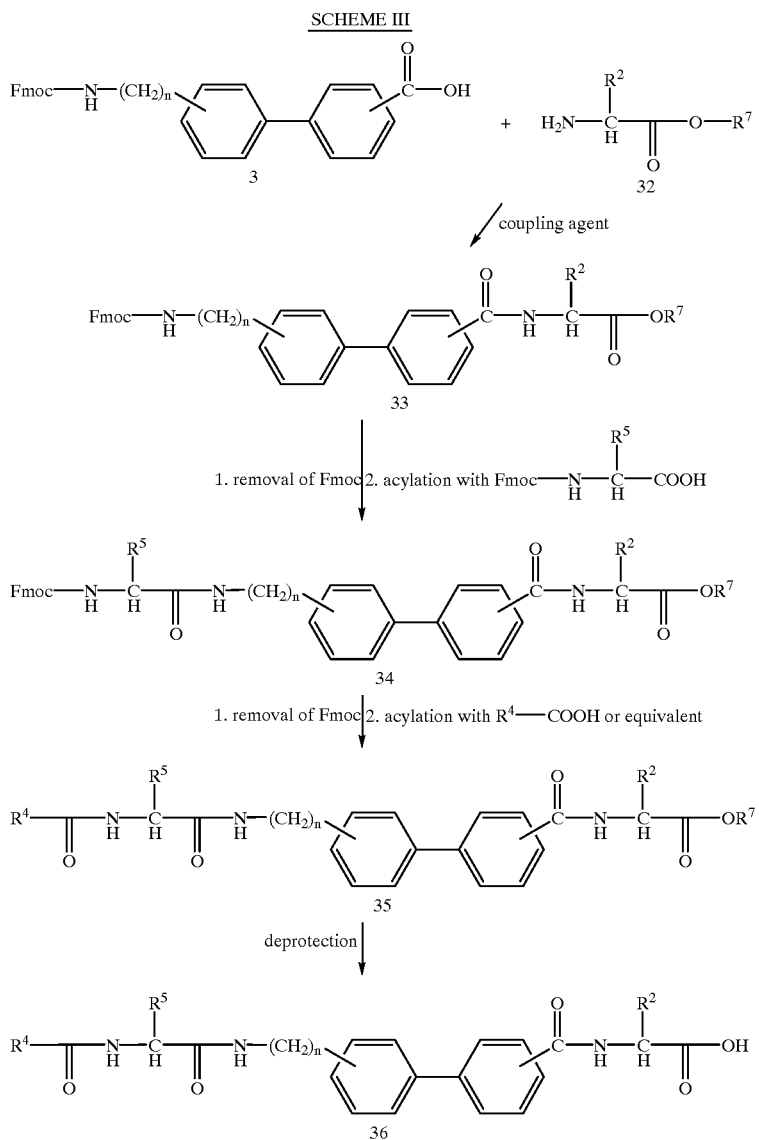

In Scheme III, compound 3, wherein n is 0 or 1 is reacted with compound 32 (wherein $R^2$ is as previously defined above, and $R^7$ is a removable protective group, e.g., t-butyl) and a coupling agent as described in Scheme I to form amide compound 33. Amide compound 33 is subjected to the same Fmoc removal/acylation steps as described in Scheme I above to produce compound 35. The protective group $R^7$ is then removed by conventional means to yield the desired compound 36. For example, t-butyl may be removed by TFA or by HCl/dioxane.

The compounds of the invention having formula (II) can be made according to Schemes I, II and III above by using the following compounds in place of compound 3 in Schemes I, II and III:

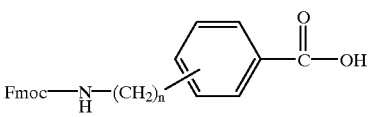

wherein n is 0 or 1. These starting compounds are known materials.

Those skilled in the art will recognize that reactive groups in the foregoing reaction schemes (e.g., carboxyl, amino, hydroxy) may be protected if desired or necessary with conventional protecting groups that can be subsequently removed by standard procedures. See, e.g., McOmie, Protecting groups In Organic Chemistry, Plenum Press, New York, 1973, and Greene and Wuts, Protecting Groups In Organic Synthesis, 2nd Ed., John Wiley & Sons, New York 1991.

For preparing pharmaceutical compositions from the compounds of this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Opthalmic preparations may be formulated using commercially available vehicles such as Sorbi-care® (Allergan) or Neodecadron® (Merck, Sharp & Dohme).

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from 0.01 mg to 1000 mg, more preferably from 0.1 mg to 200 mg, most preferably from 5 mg to 100 mg, according to the particular application.

The actual dosage employed may be varied depending upon the requirements of the patient and the severity of the condition being treated. Determination of the proper dosage for a particular situation is within the skill of the art Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention will be regulated according to the judgment of the attending clinician considering such factors as age, condition and size of the patient as well as severity of the symptoms being treated. A typical recommended dosage regimen is oral administration of from 0.02 mg to 4,000 mg/day, preferably 0.2 mg to 800 mg/day, most preferably 10 mg to 400 mg/day in two to four divided doses to block tumor growth.

The following examples illustrate the foregoing invention, although such examples should not be construed as limiting the scope of the invention. Alternative mechanistic pathways and analagous structures within the scope of the invention will be apparent to those skilled in the art.

EXAMPLES

The following resin reagents are used for the preparations below:

2-Chlorotrityl resin, chloride form, " CT resin ":

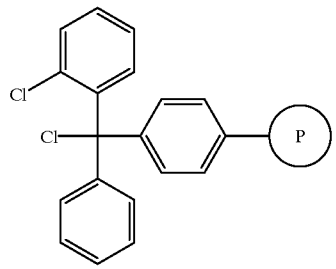

Sasrin Resin, " Sasrin Resin ":

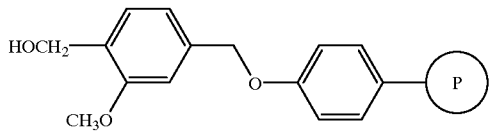

Rink Amide MBHA Resin, " Rink Amide Resin ":

-continued

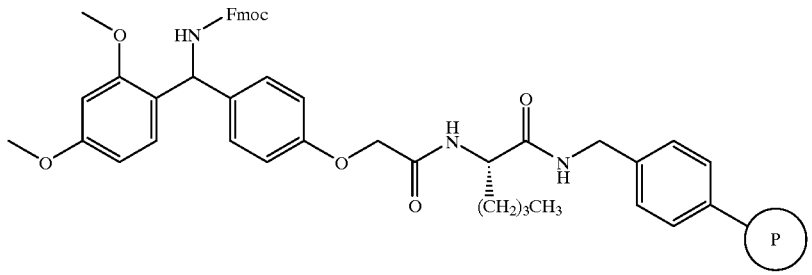

The symbol

represents the resin (polymer) portion of the resin reagent. Thus, e.g., assayed on an HPLC. HPLC is carried out under the following conditions: Vydac column [218TP54], at 1 mL/minute, UV detection 254 nM:

condition (a) 25–80% MeCN—$H_2O$ gradient (0.1% TFA) over 40 minutes condition (a) 25–90% MeCN—$H_2O$ gradient (0.1% TFA) over 40 minutes.

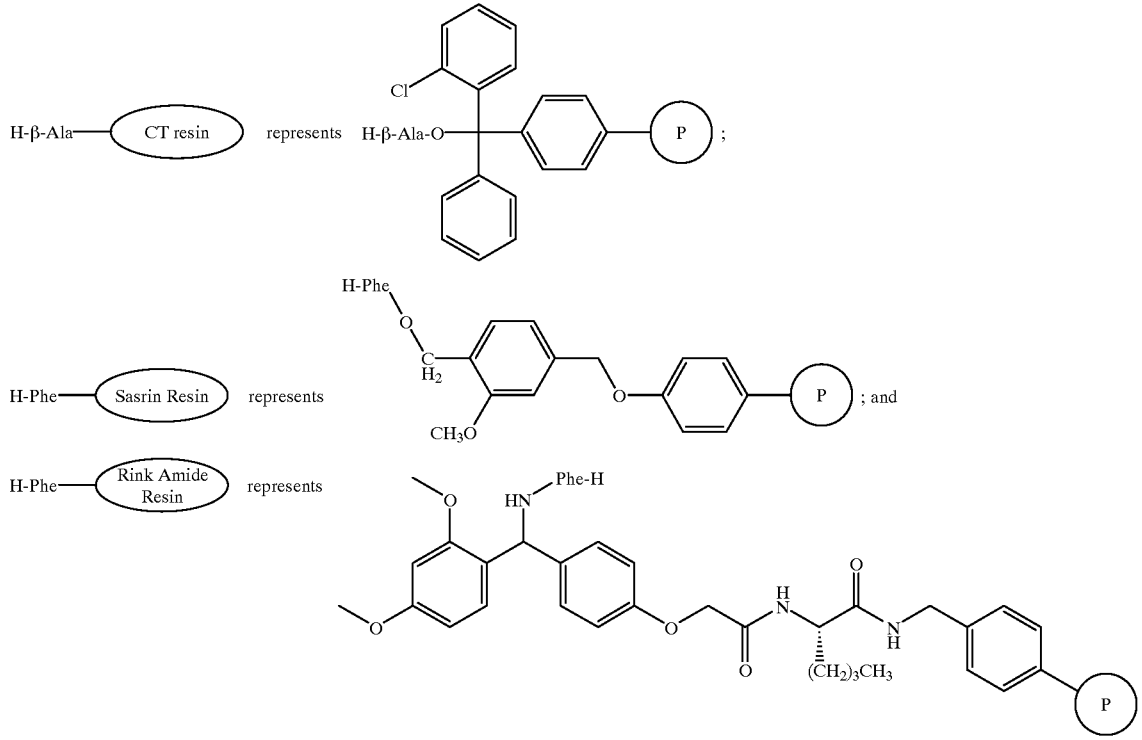

For preparations 1–3 and the numbered Examples below, a funnel apparatus is used to carry out the reactions and all washings of the resins, except for the reactions described in Examples 3, 5, 6, and 7. The funnel apparatus is a sintered glass funnel for agitating the contents with nitrogen and removal of the solvent by filtration. The resins are washed, e.g., (20 mL×5), by agitating the resin in solvent (20 mL) with nitrogen in a funnel apparatus for two minutes, removing the solvent by filtration (drain), and repeating the sequence 4 additional times.

For Examples that involve monitoring the reaction by HPLC, the resin (trace) is treated with $CH_2Cl_2$:TFA:$H_2O$ (99: 0.95 : 0.05) for 15 minutes, filtered, and the filtrate is Preparation A 4'-(Fmoc-amino)biphenyl-4-carboxylic acid

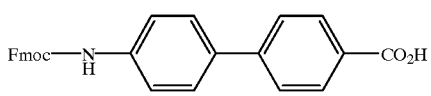

Step 1. 4'-Nitrobiphenyl-4-carboxylic acid

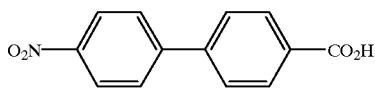

To a mixture of concentrated HNO3 and fuming HNO3 (425 mL each) at 0° C., add biphenyl-4-carboxylic acid (78.0 g, 0.39 mol). Stir 45 minutes and pour into ice-water (2.0 L). Filter the solid, wash with water, and dry. Boil with EtOH (2.0 L), filter hot, and allow to cool. Filter to obtain yellow solid (61 g). Boil with CH2Cl2—MeOH (1:1, 4.0 L) and filter to obtain the title compound (34.4 g) as a yellow solid, m.p.>300° C.

Step 2. 4'-Aminobiphenyl-4-carboxylic acid

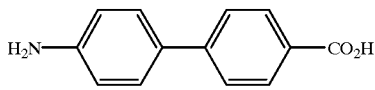

Treat the above nitro-acid (Preparation A, Step 1) with MeOH (1.0 L) and 1.0N NaOH (400 mL) and filter to remove insoluble solid (3.7 g). Add PtO2 (0.9 g) and hydrogenate at 40 psi for 15 minutes. Filter through CELITE® filter agent, concentrate to 400 mL, and add 1.0N HCl (400 mL). Filter, wash with water, and dry to obtain the title compound (19.8 g) as a beige solid, m.p. 245–8° C.

Step 3. 4'-(Fmoc-amino)biphenyl-4-carboxylic acid

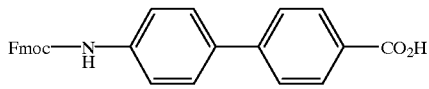

Combine the above solid (Preparation A, Step 2) (0.80 g, 3.75 mmol) with Na2CO3 (0.99 g, 9.4 mmol) in dioxane (15 mL) and water (18 mL). Cool to 0 ° C. and add Fmoc-Cl (0.97 g, 3.75 mmol) in dioxane (20 mL). Stir 18 hours without cooling and partition between EtOAc and 1.0N HCl. Dry (MgSO$_4$) and concentrate the EtOAc to obtain beige solid (0.77 g). Boil the solid with hexane (50 mL), allow to cool, and filter to obtain the title compound as a tan solid.

Preparation B

3'-(Fmoc-amino)biphenyl-4-carboxylic acid

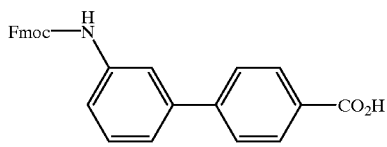

Step 1. Ethyl 3'-nitrobiphenyl-4-carboxylate

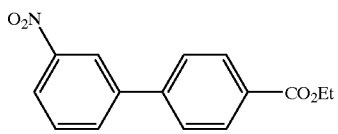

Add Pd[P(Ph)3]4 (0.35 g, 0.3 mmol) and 2M aqueous Na2CO3 (10 mL) to a solution of 3-nitrophenylboronic acid (1.84 g, 11.0 mmol ) and ethyl 4-bromobenzoate (2.3 g, 10.0 mmol ) in a mixture of EtOH (5 mL) and toluene (25 mL) under N2. Reflux, with vigorous stirring, overnight. Cool, dilute with EtOAc (3 volumes), and wash with water. Dry (MgSO4), and strip solvent in vacuo. Recrystallle the residue from EtOH to give the title compound, m.p. 110–111.5° C. MS (Cl$^+$/CH4) m/z 272 [M+H]$^+$.

Step 2. 3'-Nitrobiphenyl-4-carboxylic acid

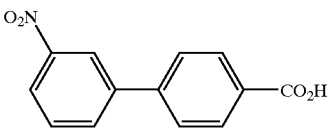

Heat under reflux ethyl 3'-nitrobiphenyl-4-caboxylate (Preparation B, Step 1) (1.36 g, 5 mmol) in MeOH (50 mL) containing 87% KOH (1.94 g, 30 mmol ) for 6 hours; allow to cool and stir overnight. Strip solvent in vacuo, take up the residue in water (75 mL), and acidify with 10% aqueous HCl to give the title product, crystalline, m.p. >300° C. MS (Cl$^+$/CH4) m/z 244 [M+H]$^+$.

Step 3. 3'-Aminobiphenyl-4-carboxylic acid

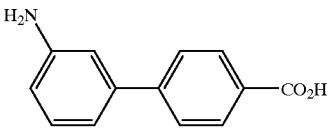

Hydrogenate 3'-nitrobiphenyl-4-carboxylic acid (Preparation B, Step 2) (1.1 g, 4.5 mmol) in water (100 mL) containing NaOH (0.2 g, 5 mmol) in the presence of 10% Pd/C catalyst (0.2 g) for 3 hours. Remove catalyst, acidify the filtrate with AcOH, collect and wash the precipitate to give the title compound. MS (Cl$^+$/CH4) m/z 214 [M+H]$^+$.

Step 4. 3'-(Fmoc-amino)biphenyl-4-carboxylic acid

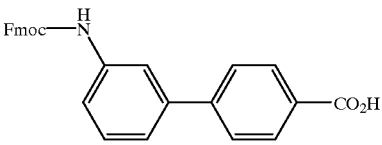

Dissolve 3'-aminobiphenyl-4-carboxylic acid (Preparation B, Step 3) (1.07 g, 5 mmol) and Na2CO3 (1.33 g, 12.5 mmol ) in H2O-dioxane (2:1, 45 mL), and cool the solution to ~3° C. Add Fmoc-Cl (1.3 g) in dioxane (10 ml); stir at ice bath temperature for 3 hours, allow to warm to room temperature and stir for another 4 hours. Pour into ice water and acidify with aqueous HCl. Extract with EtOAc. Dry extracts over MgSO4, and strip solvent in vacuo. Recrystallize residue from CH3CN to give the title compound. HPLC Retention Time, 22.6 minutes (condition (b)).

Preparation C

4'-(Fmoc-amino)biphenyl-3-carboxylic acid

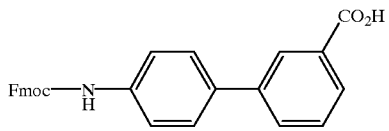

Step 1. Ethyl biphenyl-3-carboxylate

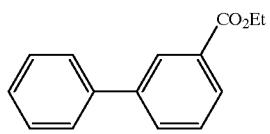

Heat under reflux a mixture of phenylboronic acid (5.4 g, 44 mmol ), ethyl 3-bromobenzoate (9.2 g, 40 mmol), and Pd[P(Ph)3]4 (1.4 g, 1.2 mmol) in a mixture of 2N aqueous Na2CO3 (40 mL) and toluene (100 mL) under N2 for 4 hours. Cool the reaction mixture, separate the aqueous layer, and wash the organic phase successively with water and brine; dry it over MgSO4. Chromatograph on silica; elute with 5% EtOAc/hexane to give the title compound. MS (Cl$^+$/CH4) m/z 227 [M+H]$^+$.

Step 2. Biphenyl-3-carboxylic acid

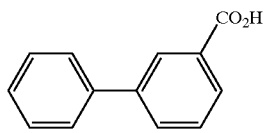

Heat under reflux ethyl biphenyl-3-carboxylate (8.3 g, 36.7 mmol) (Preparation C, Step 1) in MeOH (400 mL) containing 87% KOH (14.3 g, 222 mmol) under N2 for 3 hours. Cool and allow to stir overnight at room temperature. Strip solvent in vacuo, and take up the residue in water. Acidify with concentrated aqueous HCl to give the title product, m.p. 162–163.5° C. MS (Cl$^+$/CH4) m/z 199 [M+H]$^+$.

Step 3. 4'-Nitrobiphenyl-3-carboxylic acid

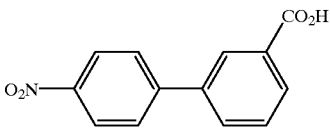

Heat under reflux biphenyl-3-carboxylic acid (Preparation C, Step 2) (5.0 g, 25 mmol) in AcOH (20 mL) containing fuming nitric acid (7 mL) for 1 hour. Cool, collect precipitate, and wash with water. Recrystallize from CH3OH, CH3CN to give title compound. HPLC; MS (Cl$^+$/CH4) m/z 243 [M+H]$^+$. [Danley, JACS 76, 4543 (1954)].

Step 4. 4'-Aminobiphenyl-3-carboxylic acid

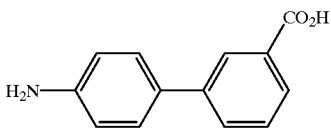

Hydrogenate 4'-nitrobiphenyl-3-carboxylic acid (Preparation C, Step 3) (4.9 g, 20 mmol) in H2O (100 mL) containing NaOH (0.9 g, 22 mmol) and 10% Pd/C catalyst (0.8 g) at 60 psi at room temp. for 3 hours. Filter off catalyst, and acidify filtrate with AcOH to give the title compound, crystalline, m.p. 225.5–228.5° C. MS (Cl$^+$/CH4) m/z 214 [M+H]$^+$.

Step 5. 4'-(Fmoc-amino)biphenyl-3-carboxylic acid

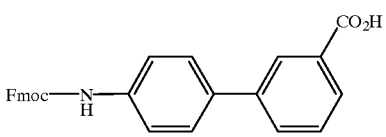

Cool a mixture of 4'-aminobiphenyl-3-carboxylic acid (Preparation C, Step 4) (7.46 g, (35 mmol) and Na2CO3 (9.3 g, 87.7 mmol) in H2O /dioxane (2:1, 300 mL) to ~5° C. Add Fmoc-Cl (9.05 g, 35 mmol), and stir the mixture at ice bath temperature for 4 hours. Allow reaction mixture to warm to room temperature and stir for 24 hours. Pour into ice water, and acidify with aqueous HCl. Collect the precipitate, wash with water, and dry in vacuo. Recrystallize from EtOAc to give the title compound, m.p. 270.5–272° C. HPLC; FAB MS m/z 436 [M+H]$^+$.

Preparation D

2'-(Fmoc-aminomethyl)biphenyl-4-carboxylic acid

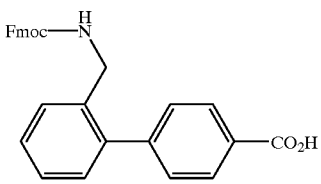

Step 1. Ethyl 2'-methylbiphenyl-4-carboxylate

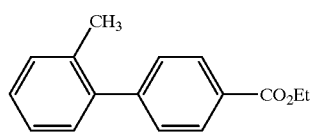

Under nitrogen, heat at reflux 2-methylphenylboronic acid (4.5 g, 33 mmol), ethyl 4-bromobenzoate (6.9 g, 30 mmol), and Pd[P(Ph)3]4 (1.04 g, 0.9 mmol) in a mixture of EtOH (15 mL), toluene (75 mL), and 2N aqueous Na2CO3 (30 mL) overnight. Cool, separate the aqueous layer, wash the organic phase, and dry (MgSO4). Remove solvent in vacuo and chromatograph the residue on silica gel. Elute with EtOAc:hexane 4:96 to give the title compound. MS (Cl$^+$/CH4) m/z 241 [M+H]$^+$.

Step 2. Ethyl 2'-bromomethylbiphenyl-4-carboxylate

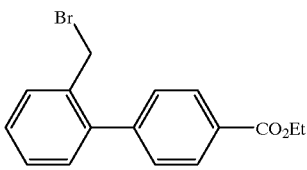

Heat under reflux ethyl 2'-methylbiphenyl-4-carboxylate (Preparation D, Step 1) (2.4 g, 10 mmol), N-bromosuccinimide (2.16 g, 12 mmol), and dibenzoyl peroxide (0.050 g) in CCl4 for 6 hours. Allow to cool, filter off succinimide, and strip solvent in vacuo. Chromatograph the residual oil on silica gel using EtOAc:hexane 1.5:98.5 as eluant to give the title compound and a minor impurity, the dibromide. Recrystallize from hexane to give the title compound. MS ($Cl^+$/CH4) m/z 319 $[M+H]^+$.

Step 3. Ethyl 2'-azidomethylbiphenyl-4-carboxylate

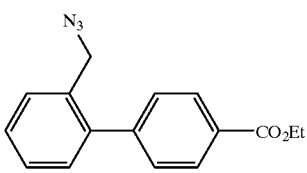

Stir ethyl 2'-bromomethylbiphenyl4-carboxylate (Preparation D, Step 2) (1.28 g, 4 mmol) in DMF (20 mL) containing sodium azide (0.3 g, 5 mmol) at room temperature for 2 days. Remove the DMF in vacuo, and partition the residue between ether and water to give the title compound. MS ($Cl^+$/CH4) m/z 282 $[M+H]^+$.

Step 4. Ethyl 2'aminomethylbiphenyl-4-carboxylate•HCl

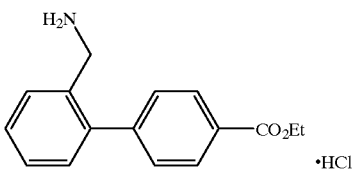

Hydrogenate ethyl 2'-azidomethylbiphenyl-4-caboxylate (Preparation D, Step 3) (8.3 g, 29.5 mmol) in EtOH (100 mL) containing 5% Pd/C catalyst at 50 psi at room temperature. Remove the catalyst by filtration, and concentrate the filtrate in vacuo to give a residue containing product and by-product, ethyl 2'-methylbiphenyl-4-carboxylate. Slurry in ether and add excess concentrated aqueous HCl to precipitate the title compound. MS ($Cl^+$/CH4) m/z 256 $[M+H]^+$.

Step 5. 2'-Aminomethylbiphenyl-4-carboxylic acid

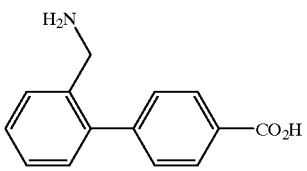

Heat under reflux ethyl 2'-aminomethylbiphenyl-4-carboxylate-HCl (Preparation D, Step 4) (1.46 g, 5.0 mmol) in a mixture of MeOH (60 mL) and 1N aqueous NaOH (17.5 mL) for 2.5 hours. Remove the MeOH in vacuo, and dilute the residue with ice-water (50 mL). Acidify with AcOH to give the title compound as a crystalline solid. MS ($Cl^+$/CH4) m/z 228 $[M+H]^+$.

Step 6. 2'-(Fmoc-aminomethyl)biphenyl-4-carboxylic acid

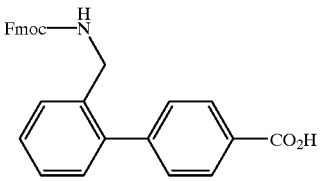

Cool to 5° C. a mixture of 2'-aminomethylbiphenyl-4-carboxylic acid (Preparation D, Step 5) (1.14 g, 5.0 mmol) and Na2CO3 (1.33 g, 12.5 mmol) in water:dioxane (2:1, 70 mL). Add Fmoc-Cl (1.3 g, 5.0 mmol) and stir at ice-bath temperature for 4 hours, then overnight at room temperature. Pour into a mixture of warm EtOAc (1 L) and 1N aqueous HCl (100 mL) and stir vigorously. Separate organic layer, dry (MgSO4), and concentrate in vacuo until solids appear. Collect the title compound, m.p. 215–218° C. MS ($Cl^+$/CH4) m/z 450 $[M+H]^+$.

Preparation 1

3-Aminopropionic acid on 2-chlorotrityl resin

Step 1a. To a solution of DIPEA (0.52 mL, 3 mmol) in CH2Cl2 (30 mL), add 3-(Fmoc-amino)propionic acid (0.47 g, 1.50 mmol). Add 2-chlorotrityl resin, chloride form (1.00 g, 0.70 mmol/g). Agitate the resulting mixture for 30 minutes. Add MeOH (0.50 mL), agitate the mixture for 10 minutes and drain. Wash the resin with DMF (30 mL×5) for 2 minutes and then CH2Cl2 (20 mL×5) to give 3-(Fmoc-amino)propionic acid on 2-chlorotrityl resin.

Step 1b. Wash the resin (Preparation 1, Step 1a) with DMF (50 mL×5). Add 50% piperidine in DMF (15 mL), agitate for 15 minutes, and collect the filtrate. Repeat two times. To determine loading level, combine filtrate in 50 mL volumetric flask, and add DMF to 50 mL (Solution A). Dilute Solution A (5.0 mL) to 100 mL in a volumetric flask (Solution B). Dilute Solution B (10 mL) to 100 mL (Solution C). Measure the UV absorbance at 301 nm: 0.252

0.252 ×concentration/7800

0.252×10,000/7800=0.323 mmol/g

Step 1c. Wash the resin (Preparation 1, Step 1b) with DMF (30 mL×5) and then CH2Cl2 (20 mL×5). Dry the resin in a vacuum oven at 40° C. for 20 hours to give title resin.

Using the same method, prepare the following resins:

-continued

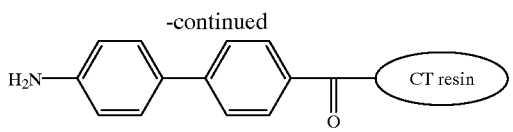

Preparation 2

Phenylalanine on Rink Amide MBHA Resin

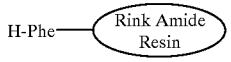

Step 1a. Wash Fmoc-Rink amide MBHA resin (NovaBiochem) (0.99 g, 0.49 mmol) with DMF (15 mL×2). Add 20% piperidine in DMF (15 mL), agitate for 5 minutes and drain. Repeat two times for 15 minutes. Wash the resin with DMF (15 mL×5) and then CH2Cl2 (20 mL×5). Transfer the resin to a vial, add CH2Cl2 (20 mL), PyBroP (1.37 g, 2.94 mmol), Fmoc-Phe-OH (1.14 g, 2.94 mmol) and DIPEA (1.03 mL, 5.88 mmol), seal the vial and place it on a shaker for 2 hours. Wash the resin with CH2Cl2 (15 mL×3), DMF (15 mL×5) and then CH2Cl2 (15 mL×5) to give Fmoc-Phe-Rink Amide resin.

Step 1b. Wash the resin (Preparation 2, Step 1a) with DMF (20 mL×2). Add 20% piperidine in DMF (15 mL), agitate for 15 minutes, and collect the filtrate. Repeat two times. To determine loading level, combine filtrate in 100 mL volumetric flask, and add DMF to 100 mL (Solution A). Dilute Solution A (1.0 mL) to 100 mL in a volumetric flask (Solution B). Measure the UV absorbance at 301 nm: 0.380

0.380 ×concentration/7800

0.380×10,000/7800=0.487 mmol/g

Step 1c. Wash the resin (Preparation 2, Step 1b) with DMF (30 mL×5) and then CH2Cl2 (20 mL×5). Dry the resin in a vacuum oven at 40° C. for 20 hours to give title resin.

Using the same method, prepare the following resin:

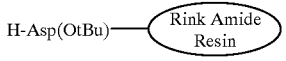

Preparation 3

Phenylalanine on Sasrin Resin

Wash Fmoc-phenylalanine on Sasrin resin (1.00 g, 0.69 mmol) with DMF (20 mL×2). Add 20% piperidine in DMF (20 mL), agitate for 5 minutes, and drain the solvent. Repeat two times for 15 minutes. Wash the residue with DMF (20 mL×5) and then CH2Cl2 (20 mL×5). Dry the resin in a vacuum oven at 40° C. for 20 hours to give title resin.

Using the same method, prepare the following resins:

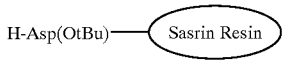

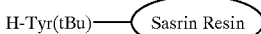

Example 1

N-[4-(4-Fmoc-aminophenyl)benzoyl]-3-aminopropionic acid on Chlorotrityl resin (HOBT/HBTU Coupling)

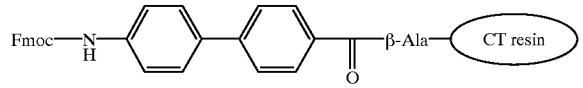

Treat 3-aminopropionic acid on chlorotrityl resin (Preparation 1) (1.00 g, 0.323 mmol) in DMF (10 mL) with a mixture of the following: 4-(4-Fmoc-aminophenyl) benzoic acid (Preparation A, 0.43 g, 0.99 mmol), 0.45M HBTU/HOBT in DMF (2.64 mL, 4 mmol), and DIPEA (0.84 mL, 16 mmol) for 90 minutes at room temperature. Wash the resin with DMF (15 mL×5) and then CH2Cl2 (15 mL×5). Monitor completion of reaction by Ninhydrin test and by HPLC. For reactions that are incomplete, repeat the coupling.

Using the same method, with resins from Preparation 1–3 and carboxylic acids from Preparation A–D, prepare the following resins:

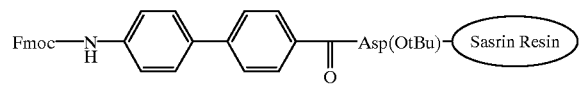

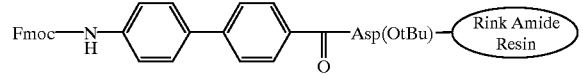

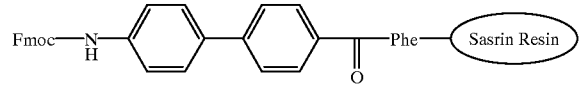

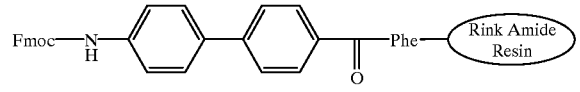

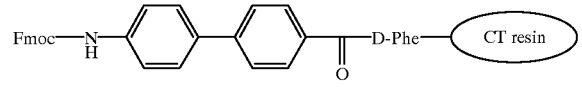

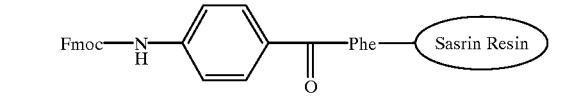

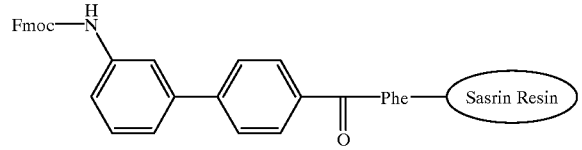

-continued

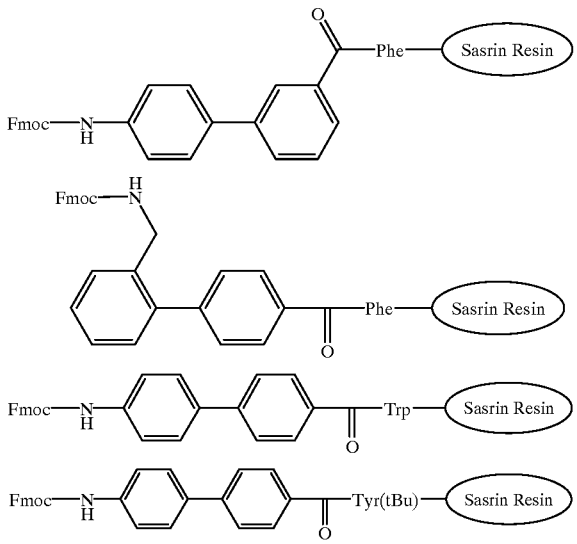

Example 2

N-[4-(4-Aminophenyl)benzoyl]-3-aminopropionic acid on Chlorotrityl resin (Removal of Fmoc Group)

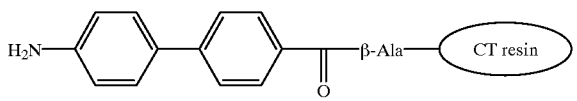

Wash the resin (Example 1, 1.00 g, 0.33 mmol) with DMF (20 mL×2). Add 20% piperidine in DMF (20 mL), agitate for 5 minutes, and drain the solvent. Repeat twice for 15 minutes. Wash the residue with DMF (20 mL×5) and then CH2Cl2 (20 mL×5) to yield the title resin.

Using the same method, prepare the following resins:

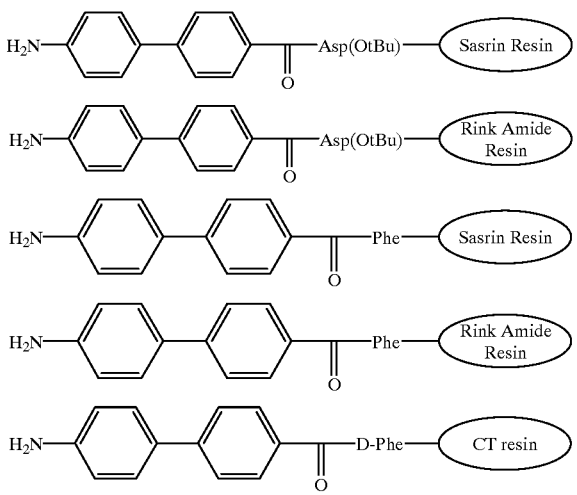

-continued

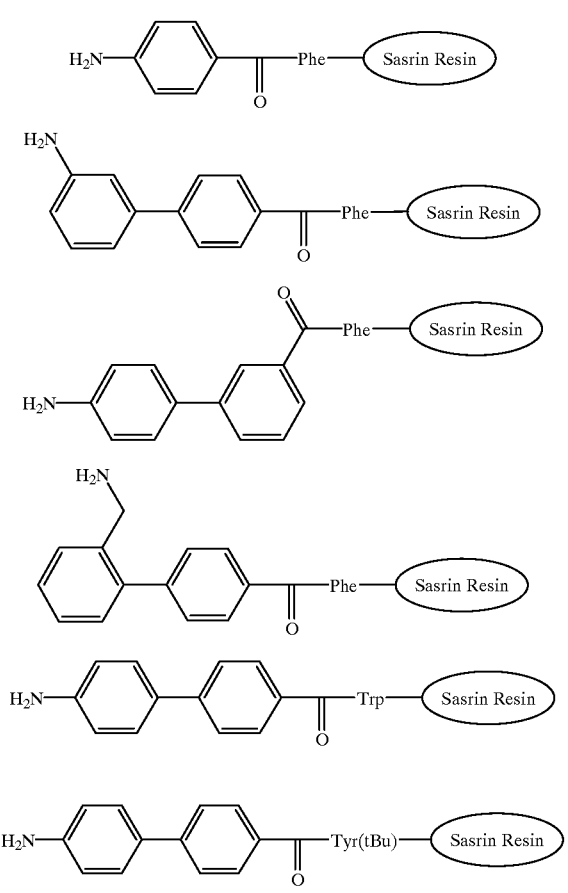

Example 3

N-[N-Fmoc-Tryptophanyl[4-(4-aminophenyl) benzoyl]]-3-aminopropionic acid on Chlorotrityl resin (PyBroP Coupling)

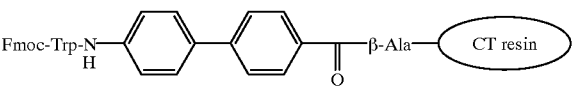

Treat the resin (Example 2) (0.33 mmol) in CH2Cl2 (15 mL) with mixture of: Fmoc-Tryptophan (1.68 g, 4 mmol), PyBroP (1.84 g, 4 mmol) and DIPEA (1.37 mL, 8 mmol). Seal the container and place on a shaker for 90 minutes. Wash the resin with DMF (20 mL×5) and then CH2Cl2 (20 mL×5). Monitor completion of reaction by Ninhydrin test and by HPLC. For sections that are incomplete, repeat the coupling.

Using the same method, prepare the following resins:
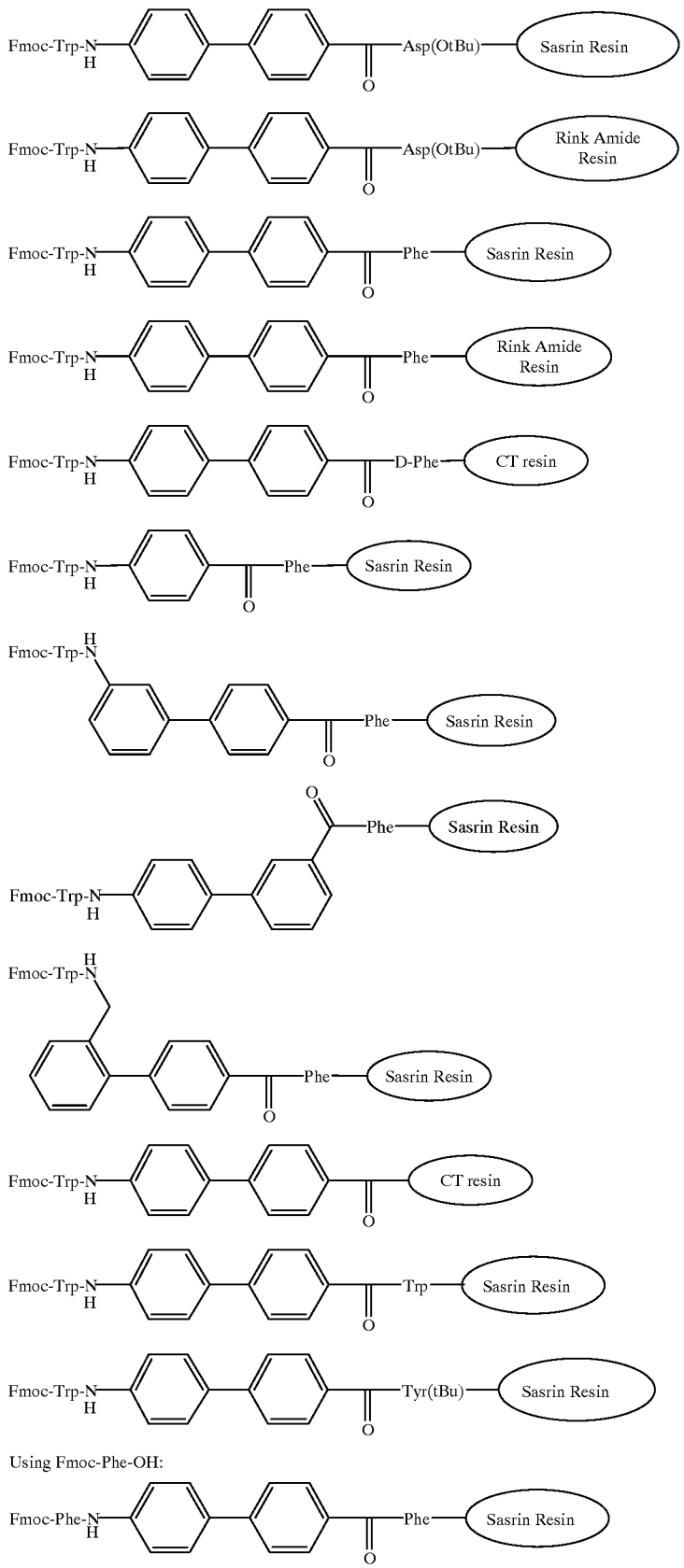
Using Fmoc-Phe-OH:

-continued
Using Fmoc-D-Trp-OH:
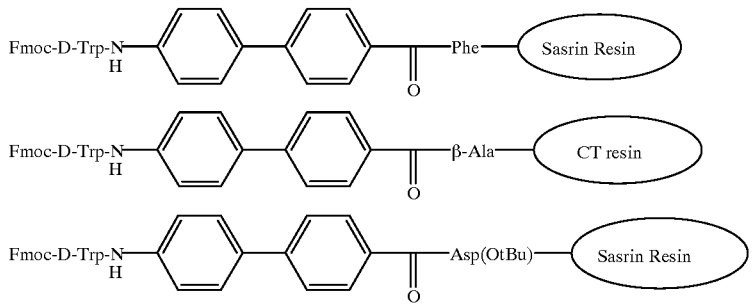
Using Fmoc-Gln(OtBu)-OH:
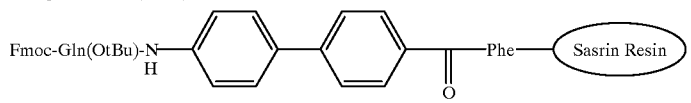
Example 4
N-[Tryptophanyl[4-(4-aminophenyl)benzoyl]]-3-aminopropionic acid on Chlorotrityl resin (Fmoc Removal)
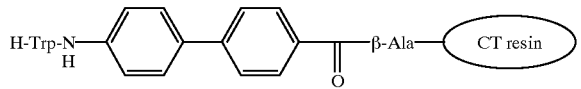
Treat resin from Example 3 as in Example 2 to give the title resin. Using the same method, prepare the following resins:
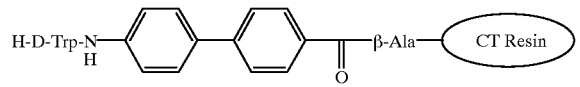
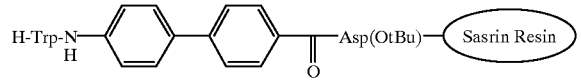
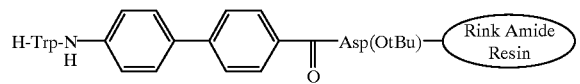
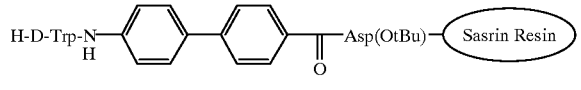
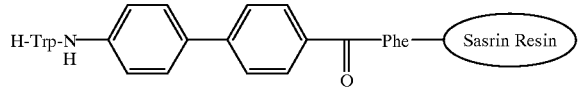
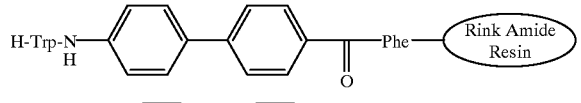
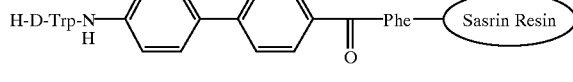
-continued
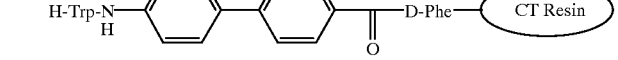
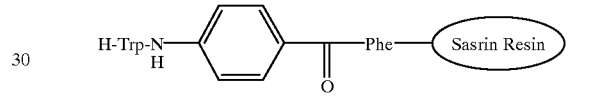
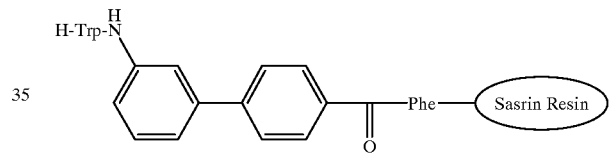
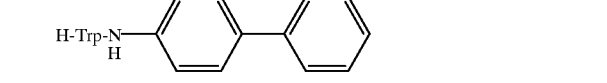
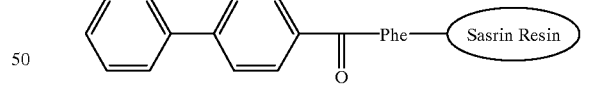
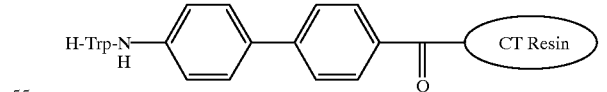
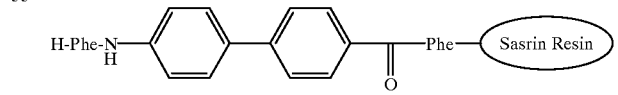
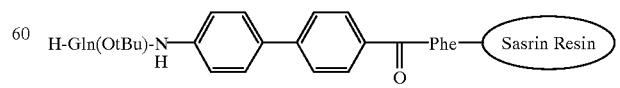

Example 5

N-[N-Acetyl[tryptophanyl[4-(4-aminophenyl)benzoyl]]-3-aminopropionic acid on Chlorotrityl resin (Acetylation)

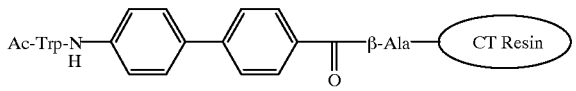

Place the resin (Example 4, 1.00 g, 0.33 mmol) in CH2Cl2 (15 mL) in a vial, and treat with DIPEA (0.57 mL, 3.3 mmol) followed by acetic anhydride (0.31 mL, 3.3 mmol). Seal the vial and place it on a shaker for 2 hours at room temperature. Place the resin in a funnel apparatus, and wash the resin with CH2Cl2 (20 mL×3), DMF (20 mL×5) and then CH2Cl2 (20 mL×5) to give the title resin.

Using the same method, prepare the following resins:

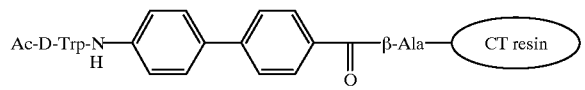
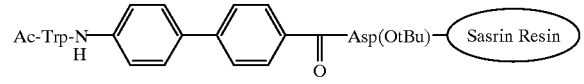
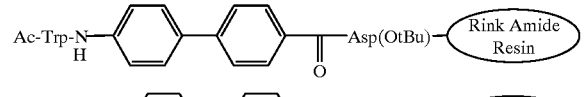
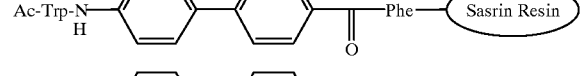
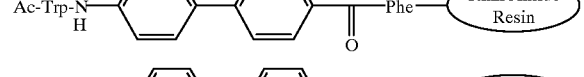
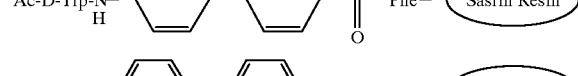
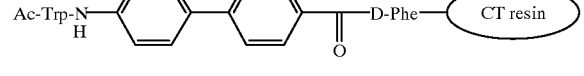

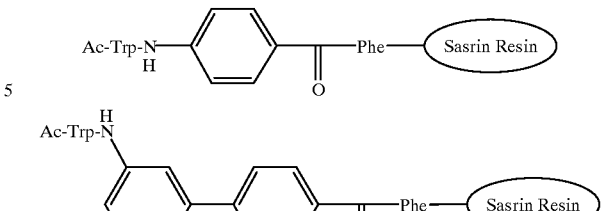
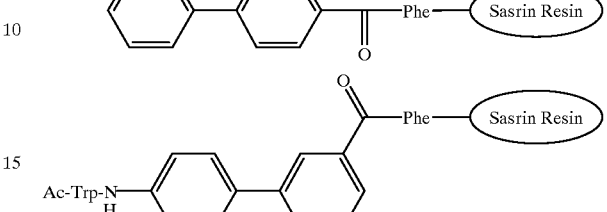
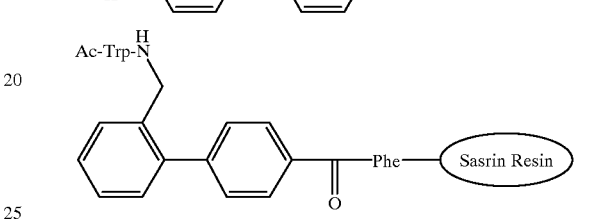
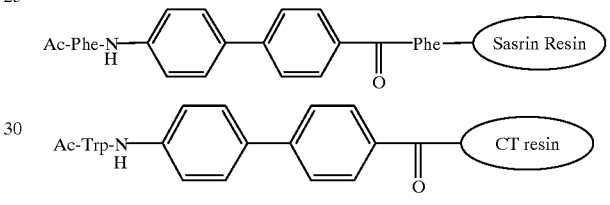
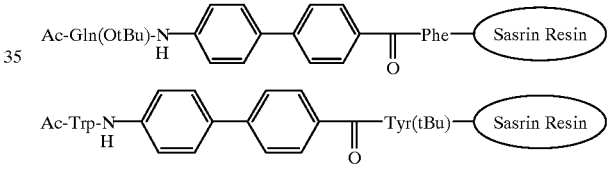
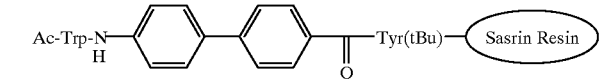
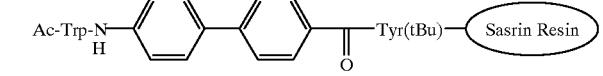

Example 6

N-[N-[3-Indolylacetyl[4-(4-aminophenyl)benzoyl]]-3-aminopropionic acid on Sasrin resin (Acylation)

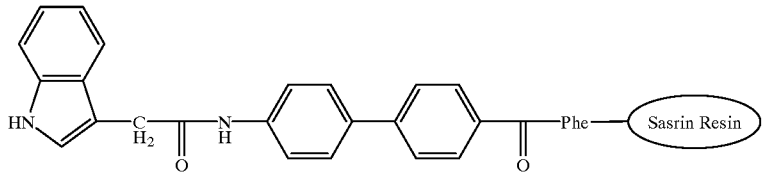

Treat the resin (Example 4, 0.33 mmol) in CH2Cl2 (5–15 mL) with a mixture of: indolyl-3-acetic acid (0.17 g, 1.0 mmol), PyBroP (0.0467 g, 1.0 mmol) and DIPEA (0.348 mL, 2.0 mmol). Seal the container and place on a shaker for 90 minutes. Wash the resin with DMF (20 mL×5) and then CH2Cl2 (20 mL×5). Monitor completion of reaction by Ninhydrin test and by HPLC. If reaction is incomplete, repeat the acylation.

Example 7

N-[N-[Methoxycarbonyl[4-(4-aminophenyl)benzoyl]]-3-aminopropionic acid on Sasrin resin (Acylation with chloroformate)

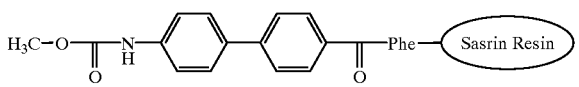

Treat the resin (Example 4, 0.30 mmol) in CH2Cl2 (15 mL) with DIPEA (0.575 mL, 3.3 mmol) and then methyl chloroformate (0.255 mL, 3.0 mmol). Seal the container and place on a shaker for 90 minutes. Wash the resin with DMF (20 mL×5) and then CH2Cl2 (20 mL×5). Monitor completion of reaction by Ninhydrin test and by HPLC. If reaction is incomplete, repeat this acylation.

Example 8

Cleavage of Products from Resin

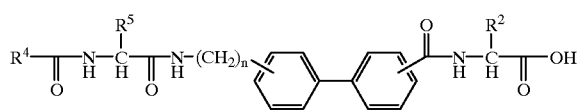

Treat the resins (Chlorotrityl or Sasrin) from Examples 3, 5–7 (~0.16 g) with CH2Cl2:TFA:H2O (99:0.95:0.05) (20 mL) at room temperature for 15 minutes and filter. Repeat this two times. Combine the filtrates, and concentrate in vacuo. Add heptane (1 mL) and concentrate in a Speed Vac. Dry the products in a vacuum oven at 40° C. for 20 hours to yield the following products:

| Example | MS m/e [M + H]+ | HPLC Retention Time, minutes (Conditions) |
|---|---|---|
| 8-A | 518 | 16.90 (a) |
| 8-B | 605 | 16.73 (a) |
| 8-C | | intermediate see Example 9 |
| 8-D | 769 | 22.46 (b) |
| 8-E | 804 | 21.93 (b) |
| 8-F | 513 | 7.60 (a) |
| 8-G | 513 | 7.60 (a) |

-continued
| Example | | MS m/e [M + H]+ | HPLC Retention Time, minutes (Conditions) |
|---|---|---|---|
| 8-H | 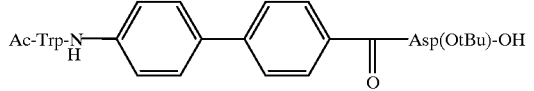 | | intermediate see Example 9 |
| 8-I | 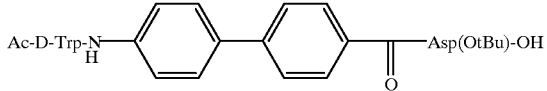 | | intermediate see Example 9 |
| 8-J | 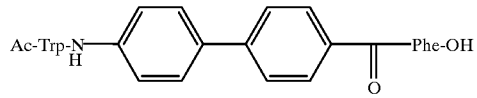 | 589 | 14.96 (a) |
| 8-K | 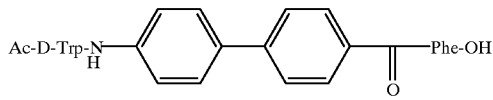 | 589 | 13.82 (b) |
| 8-L | 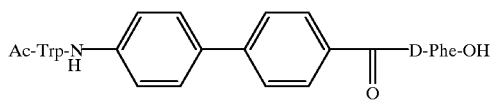 | 589 | 13.58 (b) |
| 8-M | 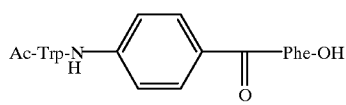 | 513 | 10.71 (b) |
| 8-N | 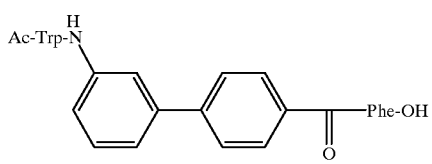 | 589 | 13.86 (b) |
| 8-O | 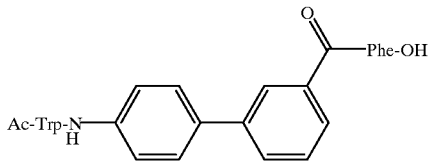 | 589 | 13.91 (b) |
| 8-P | 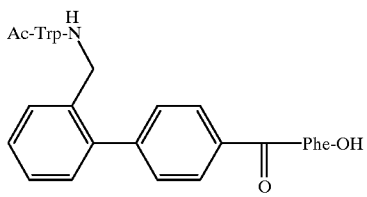 | 603 | 13.54 (b) |
| 8-Q | 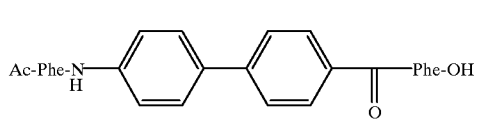 | 550 | 15.06 (a) |
| 8-R | 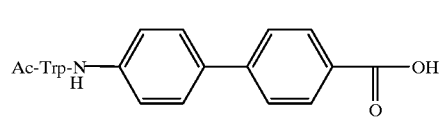 | 442 | 10.95 (b) |

-continued

| Example | | MS m/e [M + H]+ | HPLC Retention Time, minutes (Conditions) |
|---|---|---|---|
| 8-S | 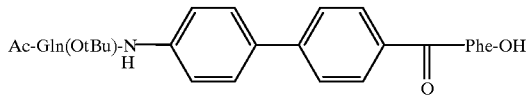 | | intermediate see Example 9 |
| 8-T | 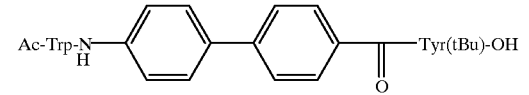 | | intermediate see Example 9 |

Example 9

Removal of Protecting Groups (Products with polar aminoacids)

Treat the product (Example 8) with 95% TFA (20 mL) for 90 minutes at room temperature. Concentrate the mixture in vacuo to just before a film. Add diethyl ether (10 mL), sonicate briefly, and filter to give a solid which is dried in a vacuum oven at 40° C. for 20 hours to give the product:

| Example | | MS m/e [M + H]+ | HPLC Retention Time, minutes (Conditions) |
|---|---|---|---|
| 9-C | 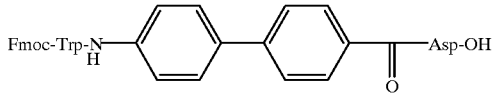 | 737 | 20.5 (a) |
| 9-H | 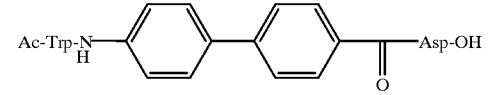 | 557 | 8.57 (a) |
| 9-I | 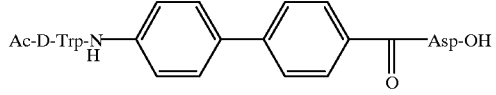 | 557 | 8.68 (a) |
| 9-S | 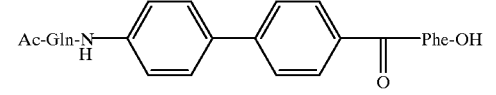 | 531 | 7.85 (a) |
| 9-T | 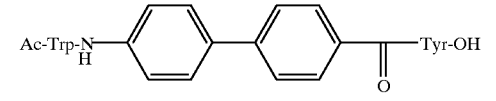 | 605 | 10.64 (b) |

Example 10

N-[N-Acetyl-[tryptophanyl[4-(4-aminophenyl)benzoyl]]-3-aminopropionic Acid Amide

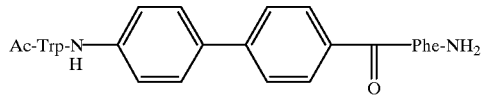

10-U

React the following resin:

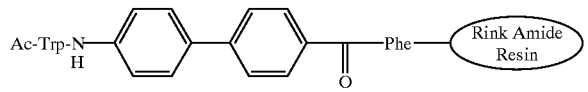

(from Example 5) with 95% TFA (20 mL) for 2 hours at room temperature. Concentrate the mixture in vacuo to a film Add diethyl ether (10 mL), sonicate briefly, and filter to give a solid which is dried in a vacuum oven at 40° C. for 20 hours to give the title product. MS m/z [M+H]$^+$588. HPLC Retention Time, 12.29 minutes (b).

Using the same method, use

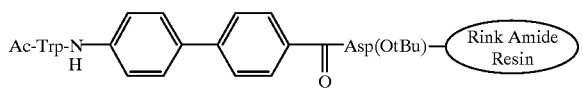

compound:

| Example | | MS m/e [M + H]$^+$ | HPLC Retention Time, minutes (Conditions) |
|---|---|---|---|
| 10-V | 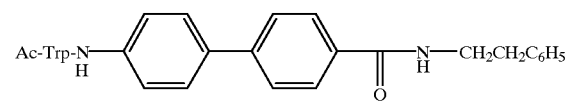 | 555 | 6.64 (b) |

Example 11

2-Phenylethyl-N-[[N-Acetyl-[trptophanyl[4-(4-aminophenyl)benzoyl]]amide

11-W

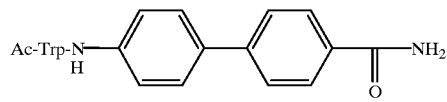

To the product from Example 8-R (0.160 g, 0.258 mmol), add 1-(3-dimethylaminopropyl)ethylcarbodiimide hydrochloride (EDC) (0.054 g, 1.1 equiv.), HOBT (0.034 g, 1.1 equiv.), DIPEA (0.09 mL, 2 equiv.), and 2-phenylethylamine (0.033 mL, 1 equiv.). Stir the resulting mixture for 20 hours. Add additional EDC (0.054 g), HOBT (0.034 g), DIPEA (0.09 mL), and 2-phenylethylamine (0.33 mL) and stir the resulting mixture for 3 days.

Concentrate the reaction mixture in vacuo. Add EtOAc (100 mL) and wash successively with water (50 mL), 1N HCl (50 mL), saturated NaHCO3 solution (2×50 mL), and brine (50 mL). Filter the dried (MgSO4) EtOAc, concentrate in vacuo to half volume, and leave overnight to give the title compound as a fluffy white solid, m.p.>230° C. MS m/z [M+H]$^+$545. HPLC Retention Time, 15.93 minutes (b).

Example 12

N-[[N-Acetyl-[trptophanyl[4-(4-aminophenyl)benzoyl]]amide

12-X

To the product from Example 8-R (0.190 g, 0.306 mmol) in dry DMF (10 mL), add DIPEA (0.059 mL, 1.1 equiv.), cool in ice bath and add ethyl chloroformate (0.027 g, 1.1 equiv.). After 15 minutes, add 28% NH4OH (0.024 mL, 1 equiv.), warm to room temperature and monitor by HPLC. After 4 hours, add DIPEA, ethyl chloroformate and 28% NH4OH as above. Repeat additions. After another 2 hours, add water (100 mL) and collect a tan precipitate. Suspend this solid in MeOH and filter to give the title compound, m.p. >230° C. MS m/z [M+H]$^+$441. HPLC Retention Time, 8.77 minutes (b).

The following assay procedure, which is a cell-based, competition radioligand binding assay, was carried out to determine the activity of the foregoing compounds as uPAR antagonists.

Radioligand Preparation. The minimal receptor-binding sequence of uPA was determined by Apella et al., *J. Biol. Chem.* 262:4437–4440 (1987), utilizing non-radioactive peptides as competition for a larger uPA radioligand. Our assay was developed and characterized using an iodinated version of the minimal receptor binding sequence of human uPA (residues 12–32, Ala[19]). The 21-amino acid peptide (cyclized), referred to herein as "c-ATFp", was synthesized and iodinated as follows: 10 ug of c-ATFp was iodinated with 1 mCi Na[125]I, using the Chloramine-T method (Iodo-Beads, Pierce Chemical Co.); iodinated peptide was separated from unincorporated iodine with Sep-Pak C18 cartridges (Millipore), and the C18-bound peptide was eluted with acetonitrile. This procedure routinely yielded a radio-iodinated c-ATFp (c-[$^{125}$I-Tyr$^{24}$]-ATFp) with specific activity of 105 Ci/mmol:

Determination of Radioligand Binding. DU-145, a human prostate cancer cell line, was selected for radioligand binding assays because these cells express high levels of unoccupied uPA receptors (approximately 500,000 receptors/cell). Subconfluent, 2 day cultures of DU-145 cells were prepared for radioligand binding assays by harvesting monolayers with trypsin/EDTA. The cells were washed one time with serum-free Dulbecco's Modified Eagle Medium (DMEM), and suspended at a cell density of 250,000 cells/ml in ice-cold DME containing 0.1% bovine serum albumin. Test compounds were solubilized in DMSO at 2 mg/ml and subsequently diluted in phosphate buffered saline to prepare stock concentrations of 200 ug/ml, 20 ug/ml, 2 ug/ml, 0.2 ug/ml, and 0.02 ug/ml. The binding reactions were initiated by addition of 1.0 ml cell suspension to microcentrifuge tubes containing 10 ul of: the indicated test compound solutions, or appropriately diluted DMSO controls, and c-[$^{25}$]-Tyr$^{24}$]-ATFp, such that the final concentration of radioligand was 3 nM (1.5 Kd). To control for specific binding, parallel reaction tubes were prepared containing 1,000-fold excess unlabeled c-ATFp. Reaction tubes were incubated with rocking at 4° C. for 90 min. Binding was terminated by 4° C. centrifugation at 800× g for 1 min in a refrigerated microcentrifuge. Unbound radioligand was removed by aspirating the reaction medium, adding fresh, ice-cold DMEM, 0.1% bovine serum albumin to the pelleted cells, and then quickly re-centrifuging and aspirating the wash from the cell pellet. The washing steps were completed in 2–4 minutes by this method, depending on the number of tubes in each experiment. Tips of microcentrifuge tubes containing the cell pellets were snipped and transferred to counting tubes. Radioactivity bound to the cells was determined in a gamma counter.

Specific binding of the radioligand was calculated as the difference between the amount of c-[$^{125}$I-Tyr$^{24}$]-ATFp bound in the absence (total binding) and presence (non-specific binding) of the unlabeled c-ATFp. The efficacy of test compounds for inhibiting specific binding of c-[$^{125}$I-Tyr$^{24}$]-ATFp was determined by plotting a graph of specific binding (y-axis) as a function of test compound concentration (x-axis). The concentration of test compound required to inhibit 50% of the specific binding (IC$_{50}$) was determined from the plot. The IC$_{50}$ may be directly converted mathematically to Ki, which is a measure of the receptor binding affinity of the compounds under the defined assay conditions. Test compounds were evaluated in duplicate tubes, in 2–3 independent binding experiments.

The uPAr IC$_{50}$ values determined by the foregoing assay for the compounds identified in the preceding examples are summarized in the table below.

| Example | | IC$_{50}$ nM |
|---|---|---|
| 8-A | | 20 |
| 8-B | | 24 |
| 9-C | | 300 |
| 8-D | | 190 |
| 8-E | | 310 |

-continued

| Example | | IC$_{50}$ nM |
|---|---|---|
| 8-F | Ac-Trp-NH—C$_6$H$_4$—C$_6$H$_4$—C(O)—β-Ala-OH | 0.9 |
| 8-G | Ac-D-Trp-NH—C$_6$H$_4$—C$_6$H$_4$—C(O)—β-Ala-OH | 18 |
| 9-H | Ac-Trp-NH—C$_6$H$_4$—C$_6$H$_4$—C(O)—Asp-OH | 60 |
| 9-I | Ac-D-Trp-NH—C$_6$H$_4$—C$_6$H$_4$—C(O)—Asp-OH | 17 |
| 8-J | Ac-Trp-NH—C$_6$H$_4$—C$_6$H$_4$—C(O)—Phe-OH | 1.8 |
| 8-K | Ac-D-Trp-NH—C$_6$H$_4$—C$_6$H$_4$—C(O)—Phe-OH | 4 |
| 8-L | Ac-Trp-NH—C$_6$H$_4$—C$_6$H$_4$—C(O)—D-Phe-OH | 8 |
| 8-M | Ac-Trp-NH—C$_6$H$_4$—C(O)—Phe-OH | 28 |
| 8-N | Ac-Trp-NH—C$_6$H$_4$(3-)—C$_6$H$_4$—C(O)—Phe-OH | 0.8 |
| 8-O | Ac-Trp-NH—C$_6$H$_4$—C$_6$H$_4$(3-C(O)—Phe-OH) | 167 |
| 8-P | Ac-Trp-NH—CH$_2$—C$_6$H$_4$—C$_6$H$_4$—C(O)—Phe-OH | 70 |

| Example | Structure | IC$_{50}$ nM |
|---|---|---|
| 8-Q | Ac-Phe-NH—C$_6$H$_4$—C$_6$H$_4$—C(O)—Phe-OH | 18 |
| 8-R | Ac-Trp-NH—C$_6$H$_4$—C$_6$H$_4$—C(O)—OH (intermediate-see Examples 11 and 12) | 1500 |
| 9-S | Ac-Gln-NH—C$_6$H$_4$—C$_6$H$_4$—C(O)—Phe-OH | 6 |
| 9-T | Ac-Trp-NH—C$_6$H$_4$—C$_6$H$_4$—C(O)—Tyr-OH | 3 |
| 10-U | Ac-Trp-NH—C$_6$H$_4$—C$_6$H$_4$—C(O)—Phe-NH$_2$ | 44 |
| 10-V | Ac-Trp-NH—C$_6$H$_4$—C$_6$H$_4$—C(O)—Asp-NH$_2$ | 1.3 |
| 11-W | Ac-Trp-NH—C$_6$H$_4$—C$_6$H$_4$—C(O)—NH—CH$_2$CH$_2$C$_6$H$_5$ | 355 |
| 12-Y | Ac-Trp-NH—C$_6$H$_4$—C$_6$H$_4$—C(O)—NH$_2$ | 91 |

The following are examples of pharmaceutical dosage forms which contain a compound (i.e., "active compound") of the invention. The scope of the invention in its pharmaceutical composition aspect is not to be limited by the examples provided.

Pharmaceutical Dosage Form Examples

Example 13

Tablets

| No. | Ingredients | mg/tablet | mg/tablet |
|---|---|---|---|
| 1. | Active compound | 100 | 5 |
| 2. | Lactose USP | 122 | 40 |
| 3. | Corn Starch, Food Grade, as a 10% paste in Purified Water | 30 | 25 |
| 4. | Corn Starch, Food Grade | 45 | 25 |
| 5. | Magnesium Stearate | 3 | 5 |
|  | Total | 300 | 100 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

Example 14

Capsules

| No. | Ingredient | mg/capsule | mg/capsule |
|---|---|---|---|
| 1. | Active compound | 100 | 5 |
| 2. | Lactose USP | 106 | 45 |
| 3. | Corn Starch, Food Grade | 40 | 45 |
| 4. | Magnesium Stearate NF | 7 | 5 |
|  | Total | 253 | 100 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound having the formula:

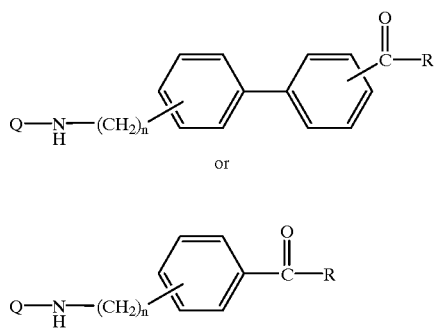

wherein n is 0 or 1;
R is —NH$^2$ or

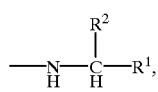

wherein $R^1$ and $R^2$ are independently selected from the group consisting of H, alkyl, aralkyl, heteroaralkyl, carboxy, carboxyalkyl, and carbamoyl;

Q is $R^3$ C(O)— or

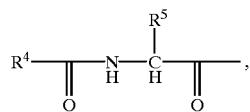

wherein $R^5$ is selected from the group consisting of H, alkyl, aralkyl, heteroaralkyl, and carbamoylalkyl, and $R^3$ and $R^4$ are selected from the group consisting of H, alkyl, alkoxy, arylalkoxy, aralkyl, heteroaralkyl, and carbamoylalkyl;

the Q-NH—(CH$_2$)$_n$— and the —C(O)R substituents of the compound of formula I are independently positioned ortho, meta, or para relative to the carbon atoms that form the bond between the two phenyl groups to which said substituents are bound, with the proviso that said substituents are not both positioned ortho; and the Q-NH—(CH$_2$)$_n$— and the —C(O)R substituents of the compound of formula II are positioned meta or para to each other;

or a biolabile ester thereof, or a pharmaceutically acceptable salt thereof.

2. The compound of claim 1, wherein $R^1$ and $R^2$ are selected from the group consisting of H, benzyl, —CH$_2$C(O)OH, p-hydroxybenzyl, —C(O)OH, —C(O)NH$_2$, and

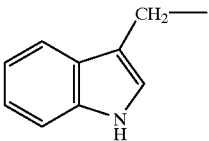

3. The compound of claim 1, wherein $R^4$ is selected from the group consisting of methyl or

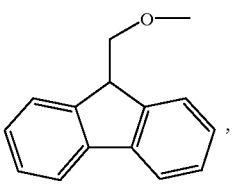

and $R^5$ is selected from the group consisting of benzyl, —CH$_2$CH$_2$C(O)NH$_2$, and

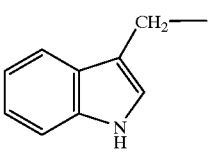

4. The compound of claim 3, wherein $R^1$ and $R^2$ are selected from the group consisting of H, benzyl, —CH$_2$C(O)OH, p-hydroxybenzyl, —C(O)OH, —C(O)NH$_2$, and

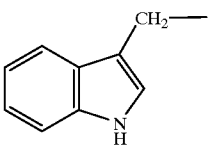

5. The compound of claim 1, wherein Q is $R^3$C(O)—.

6. The compound of claim 1, wherein $R^3$ is selected from the group consisting of methoxy and

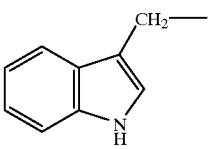

7. The compound of claim 1, wherein said compound is selected from the group consisting of

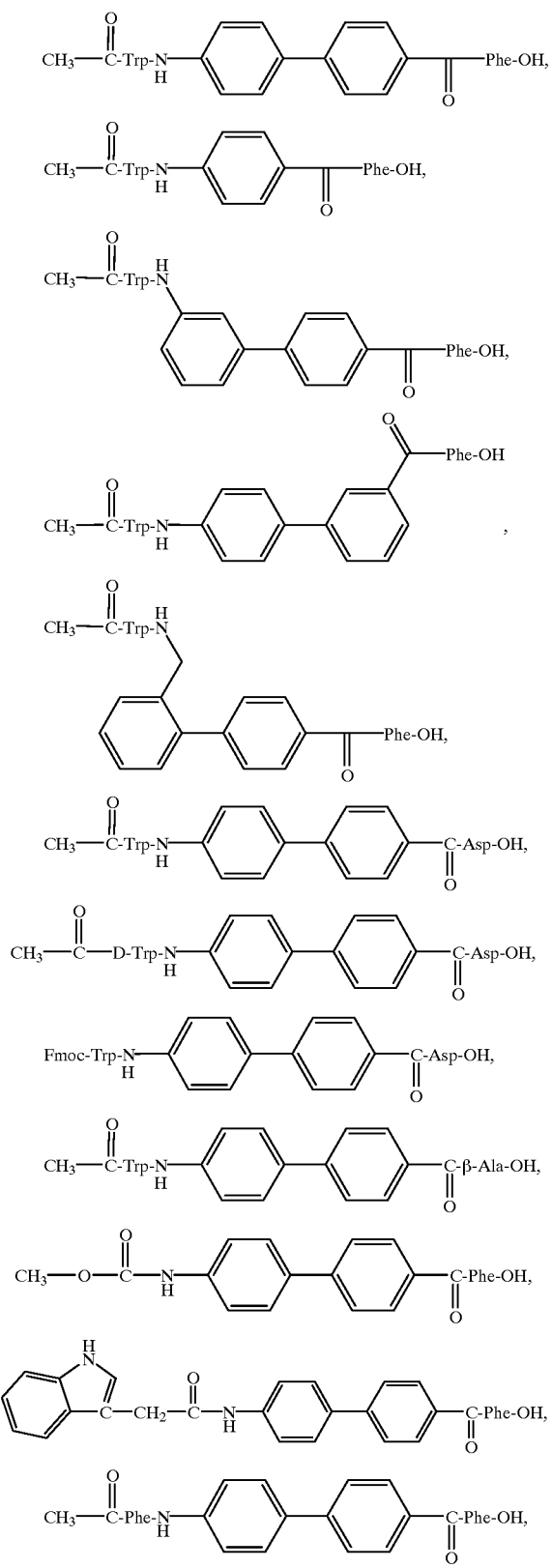
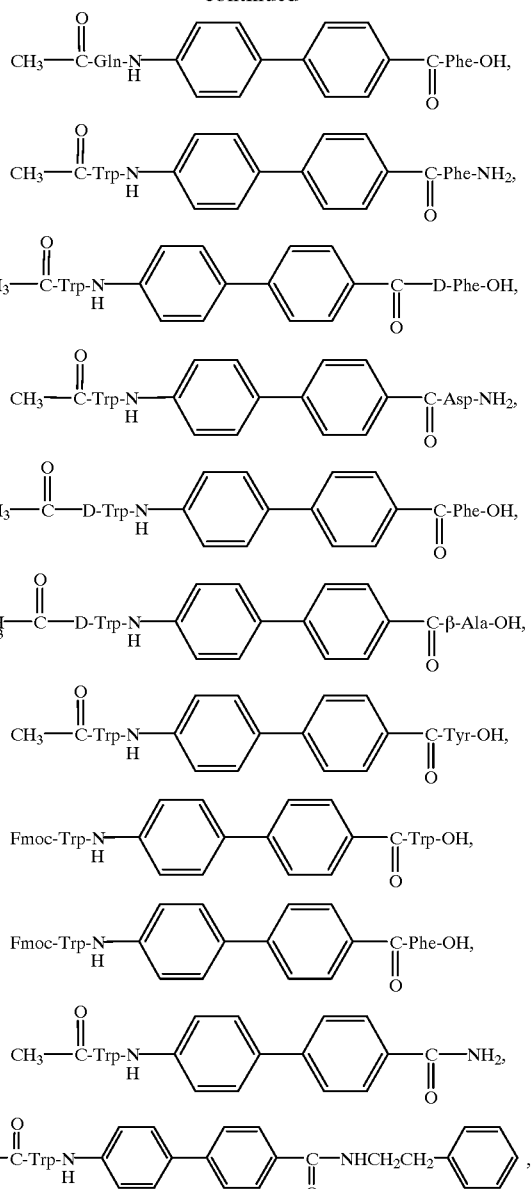
or a biolabile ester thereof, or a pharmaceutically acceptable salt thereof.
8. A pharmaceutical composition comprising the compound of claim 7 together with a pharmaceutically acceptable diluent or carrier.
9. A pharmaceutical composition comprising the compound of claim 1 together with a pharmaceutically acceptable diluent or carrier.
* * * * *